(12) United States Patent
Gombrich et al.

(10) Patent No.: US 7,838,215 B2
(45) Date of Patent: Nov. 23, 2010

(54) ADVANCED CERVICAL CELL SCREENING METHODS

(75) Inventors: Peter Gombrich, Sonoma, CA (US); Mitchell Golbus, San Rafael, CA (US)

(73) Assignee: Canvir, Inc., Novato, CA (US)

( * ) Notice: Subject to any disclaimer, the term of this patent is extended or adjusted under 35 U.S.C. 154(b) by 52 days.

(21) Appl. No.: 12/211,547

(22) Filed: Sep. 16, 2008

(65) Prior Publication Data

US 2009/0104597 A1 Apr. 23, 2009

Related U.S. Application Data

(60) Provisional application No. 60/975,069, filed on Sep. 25, 2007, provisional application No. 60/992,892, filed on Dec. 6, 2007.

(51) Int. Cl.
*C12Q 1/70* (2006.01)
(52) U.S. Cl. .......................................... 435/5; 435/345
(58) Field of Classification Search ................. None
See application file for complete search history.

(56) References Cited

U.S. PATENT DOCUMENTS

| | | | |
|---|---|---|---|
| 6,346,377 B1 | 2/2002 | Doorbar | |
| 6,582,704 B2 * | 6/2003 | Urban et al. | 424/204.1 |
| 7,399,467 B2 * | 7/2008 | Lu et al. | 424/130.1 |
| 7,482,142 B1 * | 1/2009 | Kornegay et al. | 435/91.1 |
| 2003/0219726 A1 | 11/2003 | Doorbar | |
| 2005/0260566 A1 | 11/2005 | Fischer et al. | |
| 2006/0029943 A1 * | 2/2006 | Hermonat et al. | 435/6 |

FOREIGN PATENT DOCUMENTS

EP 1 369 694 A1 10/2003

OTHER PUBLICATIONS

International Search Report, dated Mar. 25, 2009, from corresponding International Patent application PCT/US2008/076813.
Written Opinion of the International Searching Authority, dated Mar. 25, 2009, from corresponding International Patent application PCT/US2008/076813.

* cited by examiner

*Primary Examiner*—Ali R Salimi
(74) *Attorney, Agent, or Firm*—Hamre, Schumann, Mueller & Larson, P.C.

(57) ABSTRACT

Advanced cervical cancer screening methods that provide a molecular based process of detecting HPV-integration. The disclosed methods allow for a streamlined approach of conducting a Pap test and immunohistochemical test on the same slide. The disclosed methods provides an inexpensive, highly sensitive, specific, and detailed test that is easy to evaluate and follow-up.

1 Claim, 12 Drawing Sheets

| | | |
|---|---|---|
| HPV16 | 198...LKTSNAKAAM LAKFKELYGV SFSELVRPFK...227 | (SEQ ID NO: 32) |
| HPV18 | 205...LKVNNKQGAM LAVFKDTYGL SFTDLVRNFK...234 | (SEQ ID NO: 34) |
| HPV26 | 190...LKCSNVKAAL LSKFKTVYGV SFAELVRVFK...217 | (SEQ ID NO: 36) |
| HPV31 | 178...LKTSNGKAAM LGKFKELYGV SFMELIRPFQ...207 | (SEQ ID NO: 38) |
| HPV33 | 191...LHSSNTKANI LYKFKEAYGI SFMELVRPFK...220 | (SEQ ID NO: 40) |
| HPV35 | 184...LKCSNANAAM LAKFKELFGI SFTELIRPFK...213 | (SEQ ID NO: 42) |
| HPV39 | 195...LQSNNKKAAM LTQFKETYGL SFTDLVRTFK...224 | (SEQ ID NO: 44) |
| HPV45 | 191...LQASNKKAAM LAVFKDI YGL SFTDLVRNFK...220 | (SEQ ID NO: 46) |
| HPV51 | 184...LKSSNAKATL MAKFKELYGI SYNELVRVFK...213 | (SEQ ID NO: 48) |
| HPV52 | 194...MCENSIKTTV LFKFKETYGV SFMELVRPFK...223 | (SEQ ID NO: 50) |
| HPV58 | 191...LHNSNTKATL LYKFKEAYGV SFMELVRPFK...220 | (SEQ ID NO: 52) |
| HPV59 | 192...LHSKNKKAAM YAKFKELYGL SFQDLVRTFK...221 | (SEQ ID NO: 54) |
| HPV66 | 179...FKSSNVQGRL HFKFKEVYGV PYTELVRTFK...208 | (SEQ ID NO: 56) |
| HPV73 | 199...LQRNNAKAALL AKFKEVYGL SYMELVRPYK...228 | (SEQ ID NO: 58) |

Fig. 1A

| | | | |
|---|---|---|---|
| HPV16 | 288..ETIEK LLSKLLCVSP | MCMMIEPPKL | RSTAA..317 (SEQ ID NO: 31) |
| HPV18 | 295..LTVAK GLSTLLHVPE | TCMLIQPPKL | RSSVA..324 (SEQ ID NO: 33) |
| HPV26 | 278..TTIKN CLCMLLNVPE | TQLLIEPPKL | RSTAV..307 (SEQ ID NO: 35) |
| HPV31 | 268..ITIEK LLEKLLCIST | NCMLIQPPKL | RSTAA..297 (SEQ ID NO: 37) |
| HPV33 | 281..LTVAK LMSNLLSIPE | TCMVIEPPKL | RSQTC..310 (SEQ ID NO: 39) |
| HPV35 | 274..TTIEK LLSKLLCISA | ASMLIQPPKL | RSTPA..303 (SEQ ID NO: 41) |
| HPV39 | 285..VTVGK GLSTLLHVPE | SCMLLEPPKL | RSPVA..314 (SEQ ID NO: 43) |
| HPV45 | 281..LTVAK GLSTLLHVPE | TCMLIEPPKL | RSSVA..310 (SEQ ID NO: 45) |
| HPV51 | 274..TTIAK CLSTLVNIPQ | SQMFIEPPKL | RSTPV..303 (SEQ ID NO: 47) |
| HPV52 | 284..LTVSK LMSQLLNIPE | THMVIEPPKL | RSATC..313 (SEQ ID NO: 49) |
| HPV58 | 281..LTVAK LMSNLLSIPE | TCMIIEPPKL | RSQAC..310 (SEQ ID NO: 51) |
| HPV59 | 282..ITVAK GLSTLLHVPD | TCMLIEPPKL | RSGVA..311 (SEQ ID NO: 53) |
| HPV66 | 269..KTITK SLSSILNVPQ | EQMLIQPPKL | RSPAV..298 (SEQ ID NO: 55) |
| HPV73 | 289..LTVQK LLSSILNVTQ | ERMLIEPPRL | RSTPC..318 (SEQ ID NO: 57) |

*Fig. 1B*

| | | | | | |
|---|---|---|---|---|---|
| HPV16 | 598...GNPVYELNDK | NWKSFFSRTW | SRLSLHEDED | K-ENDGDSLP | TFKCVSGQNTNTL 649 (SEQ ID NO: 58) |
| HPV18 | 605...GNPVYEINDK | NWKCFFERTW | SRLDLHEEEE | DADTEGNPFG | TFKLRAGQNHRPL 657 (SEQ ID NO: 59) |
| HPV26 | 588...GNPVYALTDV | NWKSFFSTTW | SRLDLEEDAD | K-EN-GEPLP | AFKCVPGENTRLL 638 (SEQ ID NO: 60) |
| HPV31 | 578...GNPVYELSDK | NWKSFFSRTW | CRLNLHEEED | K-ENDGDSFS | TFKCVSGQNIRTL 629 (SEQ ID NO: 61) |
| HPV33 | 591...GNPVYAINDE | NWKSFFSRTW | CKLDLHEEED | K-ENHGGNIS | TFKCSAGENTRSLRS 644 (SEQ ID NO: 62) |
| HPV35 | 584...GNPVYGLNDK | NWKSFFSRTW | CRLNLHEEED | K-ENDGDAFP | AFKCVSGQNTRTLRD 637 (SEQ ID NO: 63) |
| HPV39 | 595...RNPVYTINDK | NWKCFFEKTW | CRLDLQQDED | EGDNDENTFT | TFKCVIGQNTRIL 647 (SEQ ID NO: 64) |
| HPV45 | 591...GNPVYEINDK | NWKCFFERTW | SRLDLHEDDE | DADTEGIPFG | TFKCVTGQNTRPL 643 (SEQ ID NO: 65) |
| HPV51 | 584...GNAVYTLNDE | NWKNFFSTTW | SRLDLEEED | K-EN-GDPMP | PFKCVPGENTRLL 634 (SEQ ID NO: 66) |
| HPV52 | 594...GNPIYEINNE | NWKSFFSRTW | CKLDLIQEED | K-ENDGVDTG | TFKCSAGKNTRSIRS 647 (SEQ ID NO: 67) |
| HPV58 | 591...GNPVYKINDE | NWKSFFSRTW | CKLGLIHEED | K-ENDGGNIS | TFKCSAGQNPRHIRS 644 (SEQ ID NO: 68) |
| HPV59 | 592...RNPVYTINDR | NWKCFFERTW | CRLDLNEEEE | DADSDGHPFA | AFKCVIGSNIRTL 644 (SEQ ID NO: 69) |
| HPV66 | 579...GNPVYELSNV | NWKCFFERTW | SRLNLDNDED | K-ENNGDSIP | TFRCVPEQNTRLL 630 (SEQ ID NO: 70) |
| HPV73 | 599...GNPLYQLTNE | NWKAFFIKTW | SKLDLTEDDD | K-ENDGDTVQ | TFKCVSGRNPRTV 650 (SEQ ID NO: 71) |

*Fig. 1C*

HPV 54/52
44LHLYLVPKRHCQYPLLALLNTPDQPIPHHVPTTPQKQSRARRRLENELESTAQTSNHT
APQTPWAVTTTGTSVTITTRTKDGTQVVVTLHL 134 (SEQ ID NO: 72)

HPV 58/33
4LHLYLVIKYPLLKLLTQRPPRPPTTKVHRGQSDDDSIYQTPETTPSTPQSIQTAPWTVDH
EEEDYTVQLTVHTKGGTCVVLKFHL 88 (SEQ ID NO: 73)

HPV 16
4LHLCLAATKYPLLKLLGSTWPTTPPRPIPKPSPWAPKKHRRLSSDQDQSQTPETPATPLS
CCTETQWTVLQSSLHLTAHTKDGLTVIVTLHP 95 (SEQ ID NO: 74)

HPV 31
4LNLYLAVTKYPLLGLLQSYQQPTTPPHRIPKPAPWAPVKVCGGRRRLLSDQEQSQSTET
PTTPTSCCEATPWTVSTVGLSVQLHAQTKQGLSVVLQLHL 102 (SEQ ID NO: 75)

HPV 35
4LNLYLAAQNYPLLKLLHSYTPTTPPRPIPKPAPWAPQKPRRQITNDFEGVPSSPTTPPSEC
DSVPWTVLTEGSTLHLTAQTKTGVVVVQLHL 96 (SEQ ID NO: 76)

HPV 51
1MYLVPAATRYPLLQLLNNYQTPQRPIPLPPAWAPKKPRHNSENDSDLLSPTPPQSPHCP
WTIQTTKYTVEVEALTLEGTKVQLRLRL 87 (SEQ ID NO: 77)

HPV 18
3LCAVPVTTRYPLLSLLNSYSTPPHRIPAPCPWAPQRPTARRRLLHDLDTVDSRRSSIVDL
STHFSVQLHLQATTKDGNSVVVTLRL 88 (SEQ ID NO: 78)

HPV 39
6LCAVPVTDRYPLLNLLPNYQTPPRPIPPQQPHAPKKQSRRRLESDLDSVQSQSPLSPTEC
PWTILTTHSTVTVQATTQDGTSVVVTLRL 94 (SEQ ID NO: 79)

HPV 67/68/66
4LHLCLVTKYPLLRLLPGYHTPQKRIPLPPPRAPKKNRRLPNDDDLTSQTSATTPSTPQSY
CADNGPWTVHRWGSSLDLSAQTKDGVCVHLTLHL 97 (SEQ ID NO: 80)

*Fig. 2*

```
HPV51:   ----------------LYR..HIVTIAVFTILLFVLCLCVLVCCLL.PLLLSQYVFAAALLILCFMFVVATSQLTTFFVYLFFYLPCLLLHLVTFLLLQ-
(SEQ ID NO: 81)
HPV69:   CNIVTSHKPICAAN..CIVTTILLVIVFVLCVCVCLLLCRLL.PLLLSIHVFAAHLLIIICFMFVVAAHLLYFYLPAFLLHFYAVILLPMG
(SEQ ID NO: 82)
HPV52:   ----------------MLGLFVFCFILLMFCAVLRPLLLSTSVYAQVLVLVLLLWSIG.SPFKVFFLYLFLYFPMFCIHCHAQYLAQLQ
(SEQ ID NO: 83)
HPV67:   ----------------MLAIFVFAFVLLGFCIVLRPLLLSIYVYALLLVLVLVLNGFIG.SPLRVFLAYLTFLYLPMMGIHLHAQYIVS--
(SEQ ID NO: 84)
HPV58:   ----------------MILPIFVWCFILFLCLCFPLLRPLVLSISIYAWLLVLVLLLWSVG.SALRIFFCYLIFLYIPMMRCIHFHAQYLTQQD
(SEQ ID NO: 85)
HPV33:   ----------------MIFVFVLCFILFLCFLGFSLLLRPLIILSISTYAWLLVLVLLLLWFVG.SPLKIFFCYLILFLYLPMMCINFHAQHMTQQE
(SEQ ID NO: 86)
HPV16:   ----------MIHLDYASTFLLACFLLCFLLGFCVLLGCLLIRPLLLVRSLLLSVSLLLSVSALLLVLIHLWTAA.S4FRCFIWIIFVVIPLFLIHTHARFLIT--
(SEQ ID NO: 87)
HPV35:   ----------MIDL.TASSFVLLCFLLGFCMLLCFLLCFLLCVLLGCLLVRSLLLVIRPIVLSVSVYATLLLIVLLVI.ILWVTVA.TPLRCFCCFLCFLYIPMGMIRAHAQYLAVQ-
(SEQ ID NO: 88)
HPV31:   ----------MIFLNISTVSIVLCFLLCFLLGFCVLLCFLLCVLLCVLLGCLLVRPIVLSVSVYATLLLIVLLLVI.ILWVIAT.SPLRCFCIYVFIYLPLFVIHTHASFLSQQ-
(SEQ ID NO: 89)
HPV73:   ----------MILCIFVFLFCVGFCLLCLCV.SLAVSVYIYPWLIVLIIITFIHVSQSLLKVFLYVLVFYIPMALVHYATLQIT-
(SEQ ID NO: 90)
HPV66:   ----------SPYIATIDFCVICVFALCFCVLCGHFV.PLLLSASLFTSCLILILFNFVVATSFFDTFLFLFFYIPTLCIYCHALMLINHL
(SEQ ID NO: 91)
HPV45:   ----------MLSLVFLLCFSVCLYCCNV.PLVQSVYVCAFAGLLVFIFIWI.TSPLTAFAVVICCYLLPMFVLHNHALHTIQ-
(SEQ ID NO: 92)
HPV18:   ----------MLSLIFLFCFCVCMVVCCHV.PLLPSVVCNCAYAAWLVFWVIWI.TSPATAFTVVFCFLLPMLLHTHAILSLQ-
(SEQ ID NO: 93)
HPV68M:  ----------------MMHVCVYWILVFIYLCMV.PLLPSVHVCAYVWIVFWIIFIWI.TTPLEVFAVVILFLLPMMVLHSFARYSMP-
(SEQ ID NO: 94)
HPV39:   ----------MILLVFLVWFGVCIYICMV.PLLPSVHVCAYVWIVFWIEILIR.TTPLEVFVYLLFFVLPMMLHRLAMDMI---
(SEQ ID NO: 95)
HPV59:   ----------MITLVFCQVCWCLLYCCNV.PLLQSVYMCAYTWLLVFVYIWI.TSSYECFLLYIFFIIPLLLYAHAILSIQ
(SEQ ID NO: 96)
```

*Fig. 3*

HPV_16:...MHQKRTAMFQ DPQERPRKLP QLCTELQTTI HDIILECVYC KQQLLRREVY
DFAFRDLCIV YRDGNPYAVC DKCLKFYSKI SEYRHYCYSL YGTTLEQQYN
KPLCDLLIRC INCQKPLCPE EKQRHLDKKQ RFHNIRGRWT GRCMSCCRSS RTRRETQL
(SEQ ID NO: 97)

HPV_59:...MARFEDPTQRPYKLPDLSTTLNIPLHDIRINCVFCKGELQEREVFEFAFNDLFI
VYRDCTPYAACLKCISFYARVRELRYYRDSVYGETLEAETKTPLHELLIRCYRCLKPLCP
TDKLKHITEKRRFHNIAGIYTGQCRGCRTRARHLRQQRQARSETLV (SEQ ID NO: 98)

HPV_39:...MARFHNPAERPYKLPDLCTTLDTTLQDITIACVYCRRPLQQTEVYEFAFSDL
YVVYRDGEPLAACQSCIKFYAKIRELRYYSDSVYATTLENITNTKLYNLLIRCMCCLKPL
CPAEKLRHLNSKRRFHKIAGSYTGQCRRCWTTKREDRRLTRRETQV (SEQ ID NO: 99)

HPV_45:...MARFDDPKQRPYKLPDLCTELNTSLQDVSIACVYCKATLERTEVYQFAFKD
LCIVYRDCIAYAACHKCIDFYSRIRELRYYSNSVYGETLEKITNTELYNLLIRCLRCQKPL
NPAEKRRHLKDKRRFHSIAGQYRGQCNTCCDQARQERLRRRRETQV (SEQ ID NO: 100)

HPV_66:...MDSIFSNTQERPRSLHHILSEVLQIPLLDLRLSCVYCKKELTSLELYRFACIELK
LVYRNNWPYAVCRVCLLFYSKVRKYRYYKYSVYGATLESITKKQLSDLSIRCYRCQCP
LTPEEKQLHCEHKRRFHYIAYAWTGSCLQCWRHTSRQATESV(SEQ ID NO: 101)

HPV_26:...MFEDPRERPRTLHELCESLNTTLQNLQVQCVYCKETLQWADVYNFAICDLR
VVYRDRSPYAACKRCVIFYSKITEYRRYTCSVYGATLEALTKKSLCNLLIRCHRCQMPL
GPEEKQRIVDEKRRFHEIAGQWKGLCTNCWRPRRQTETQV(SEQ ID NO: 102)

HPV_51:...MFEDKRERPRTLHELCEALNVSMHNIQVVCVYCKKELCRADVYNVAFTEIK
IVYRDNNPYAVCKQCLLFYSKIREYRRYSRSVYGTTLEAITKKSLYDLSIRCHRCQRPLG
PEEKQKLVDEKKRFHEIAGRWTGQCANCWQRTRQRNETQV(SEQ ID NO: 103)

FIG. 4A

HPV_82:...MFEDIRERPRTLHELCEACNTSMHNIQVLCVYCKKELCRADVYNVAFTELRI
VYRDNTPYAACKKCLMFYSRIREYRRYSRSVYGATLEAITNKSLYELLIRCHRCQRPLGP
EEKQKVVDD<u>KKRFHEIAGRWTGQC</u>ANCRKPPRQRSETQV(SEQ ID NO: 104)

HPV_52:...MFEDPATRPRTLHELCEVLEESVHEIRLQCVQCKKELQRREVYKFLFTDLRIV
YRDNNPYGVCIMCLRFLSKISEYRHYQYSLYGKTLEERVKKPLSEITIRCIICQTPLCPEEK
ERHVNA<u>NKRFHNIMGRWTGRC</u>SECWRPRPVT
(SEQ ID NO: 105)

HPV_58:...MFQDAEEKPRTLIIDLCQALETSVHEIELKCVECKKTLQRSEVYDFVFADLRI
VYRDGNPFAVCKVCLRLLSKISEYRHYNYSLYGDTLEQTLKKCLNEILIRCIICQRPLCPQ
EKKRHVDL<u>NKRFHNISGRWTGRC</u>AVCWRPRRRQTQV(SEQ ID NO: 106)

HPV_33:...MFQDTEEKPRTLIIDLCQALETTHHNIELQCVECKKPLQRSEVYDFAFADLTV
VYREGNPFGICKLCLRFLSKISEYRHYNYSVYGNTLEQTVKKPLNEILIRCIICQRPLCPQE
KKRHVDL<u>NKRFHNISGRWAGRC</u>AACWRSRRRETAL(SEQ ID NO: 107)

HPV_31:...MFKNPAERPRKLHELSSALEIPYDELRLNCVYCKGQLTETEVLDFAFTDLTIV
YRDDTPHGVCTKCLRFYSKVSEFRWYRYSVYGTTLEKLTNKGICDLLIRCITCQRPLCPE
EKQRHLDK<u>KKRFHNIGGRWTGRC</u>IACWRRPRTETQV(SEQ ID NO: 108)

HPV_35:...MFQDPAERPYKLHDLCNEVEESIHEICLNCVYCKQELQRSEVYDFACYDLCI
VYREGQPYGVCMKCLKFYSKISEYRWYRYSVYGETLEKQCNKQLCHLLIRCITCQKPLC
PVEKQRHLEE<u>KKRFHNIGGRWTGRC</u>MSCWKPTRRETEV(SEQ ID NO: 109)

HPV_18:...MARFEDPTRRPYKLPDLCTELNTSLQDIEITCVYCKTVLELTEVFEFAFKDLF
VVYRDSIPHAACHKCIDFYSRIRELRHYSDSVYGDTLEKLTNTGLYNLLIRCLRCQKPLN
PAEKLRHLNE<u>KRRFHNIAGHYRGQC</u>HSCCNRARQERLQRRRETQV (SEQ ID NO: 110)

*FIG. 4B*

HPV 16: 1 MHGDTPTLHE YMLDLQPETT DLYCYEQLND SSEEEDEIDG PAGQAEPDRA HYNIVTFCCK
61 CDSTLRLCVQ STHVDIRTLE DLLMGTLGIV CPICSQKP (SEQ ID NO: 111)

HPV 18: 1 MHGPKATLQD IVLHLEPQNE IPVDLLCHEQ LSDSEEENDE IDGVNHQHLP ARRAEPQRH
61 MLCMCCKCEA RIKLVVESSA DDLRAFQQLF LNTLSFVCPW CASQQ (SEQ ID NO: 112)

HPV 31: 1 MRGETPTLQD YVLDLQPKAT DLHCYEQLPD SSDEEDVIDS PAGQAKPDTS NYNIVTFCCQ
61 CESTLRLCVQ STQVDIRILQ ELLMGSFGIV CPNCSTRL (SEQ ID NO: 113)

HPV 33: 1 MRGHKPTLKEYVLDLYPEPTDLYCYEQLSDSSDEDEGLDRPDGQAQPATADYYIVTCCHTCNTTV
RLCVNSTASDLRTIQQLLMGTVNIVCPTCAQQ (SEQ ID NO: 114)

HPV 35: 1 MHGEITTLQDYVLDLEPEATDLYCYEQLCDSSEEEEDTIDGPAGQAKPDTSNYNIVTSCCKCEATL
RLCVQSTHIDIRKLEDLLMGTFGIVCPGCSQRA (SEQ ID NO: 115)

HPV 39: 1 MRGPKPTLQEIVLDLCPYNEIQPVDLVCHEQLGESEDEIDEPDHAVNHQHLLARRDEPQRHTIQC
SCCKCNNTLQLVVEASRDTLRQLQQLFMDSLGPVCP (SEQ ID NO: 116)

HPV 45: 1 MHGPRETLQEIVLHLEPQNELDPVDLLCYEQLSESEEENDEADGVSHAQLPARRAEPQRHKILCVC
CKCDGRIELTVESSAEDLRTLQQLFLSTLSFVCPWC (SEQ ID NO: 117)

HPV 51: 1 MRGNVPQLKDVVLHLTPQTEIDLQCYEQFDSSEEEDEVDNMRDQLPERRAGQATCYRIEAPC
CRCSSVVQLAVESSGDTLRVVQQMLMGELSLVCPCCANN (SEQ ID NO: 118)

HPV 52: 1 MRGDKATIKDYILDLQPETTDLHCYEQLGDSSDEEDTDGVDRPDGQAEQATSNYYIVTYCHSCDST
LRLCIHSTATDLRTLQQMLLGTLQVVCPGCARL (SEQ ID NO: 119)

HPV 66: 1 MHGKVPTLQE VLELAPQTE IDLQCNEQLD SSEDEDEDEI DHLLERPQQA RQAEQHKCYL
IHVPCCKCEL VVQLDIQSTK EELRVVQQLL MGALTVTCPL CASK (SEQ ID NO: 120)

HPV 68: 1 MHGPKPTVQE IVLELCPYNE IQPVDLVCHE QLGDSDDEID EPDHAVNHHQ HLLLARRDEQ
QRHRIQCLCC KCNKALQLVV EASRDNLRTL QQLFMDSLNF VCPWCATETQ (SEQ ID NO: 121)

HPV 56/57/58: 1 MHGERPSLED ITLILEEIPE IVDLHCDEQF DNSEEDTNYQ LTEPAVQAYG
VVTTCCKCHS TVRLVVECGA ADIRHLEQLF LNTLTIVCPR CV (SEQ ID NO: 122)

FIG. 5

ADVANCED CERVICAL CELL SCREENING METHODS

This application claims the benefit of U.S. Provisional Application No. 60/975,069, filed Sep. 25, 2007 and U.S. Provisional Application No. 60/992,892, filed Dec. 6, 2007, and which are incorporated herein by reference in their entirety.

FIELD

This disclosure relates generally to cell sampling, processing and screening for use in detecting abnormal tissue in the body, for example in the cervix. More specifically, this disclosure relates to methods whereby (1) collected cells and cell clusters are prepared such that the biological properties of such cells and cell clusters can be examined, and (2) those cells that have had human papillomavirus integrated into the host DNA are detected with an HPV-integration marker.

BACKGROUND

Human papillomavirus (HPV) has been studied extensively as a precursor of invasive cervical cancer and cervical intraepithelial neoplasia. Cervical cancer is the second most common cancer worldwide, and is the most common malignancy in developing countries.

Cervical cancer screening is commonly based on cytological and colposcopic analyses. The generally accepted cytological smear of the cervix (Papanicolaou test, Pap smear) has led to a reduction in the incidence of and mortality caused by cervical cancer. However, there are certain disadvantages to using the Pap smear test. One of the limitations of the conventional Pap smear includes non-representative transfer of cells. Also, due to obscuring of the abnormal cells by debris, such conventional methods can lead to an increase in false-negatives and equivocal results.

All forms of the Pap test focus on the screening for high-grade precursor lesions so that treatment can be initiated before these precursors progress into invasive cancers. To effectively differentiate and communicate the presence of cytologically and biologically distinctive grades of preneoplastic and cancerous lesions, the Bethesda System for Reporting Cervical Cytology has recommended six categories to characterize squamous cell abnormalities. The six categories include: (1) atypical squamous cell of undetermined significance (ASCUS), (2) atypical squamous cells, cannot exclude high-grade squamous lesions (ASC-H), (3) low-grade squamous intraepithelial lesions (LSIL), (4) high-grade squamous intraepithelial lesions (HSIL), (5) squamous cell carcinoma (SCC) and (6) normal. Under this system, HSIL may optionally be subcategorized as "HSIL (moderate dysplasia, CIN II)" or "HSIL (severe dysplasia, CIN III)". Colposcopy, and possible biopsy have been recommended as a follow-up test for ASC-H, LSIL, HSIL, and SCC, while HPV testing has been recommended for ASCUS.

HPV Pathogenesis

There are a large number of HPV types (>100) but only some are genitalphilic. HPV types that are found preferentially in cervical cancers have been categorized as high-risk types, as opposed to those found primarily in non-malignant lesions which have been designated as low-risk types. High-risk HPV DNA integration into the host genome plays a crucial role in HPV pathogenesis. The genes expressed by the HPV are divided into early (E) and late (L) expressing genes. This integration results in the specific disruption of the E2 viral gene and in the transcription and translation of the other E genes, starting with the E1, E4, and E5 genes. The E2 protein normally negatively regulates transcription of the E6 and E7 viral oncogenes, and as such, the loss of E2 expression results in the unregulated expression of the E6 and E7 genes in cervical cancer cells.

These oncoproteins act mainly through protein-protein interactions to disrupt pathways regulating cell cycle progression and proliferation. E6 targets p53 for degradation by the protease, which consequently abrogates the p53 transcriptional pathway and leads to the up-regulation of numerous genes normally suppressed by p53. The E7 gene product has a similar effect on the retinoblastoma (Rb) gene.

HPV Testing

The natural history of HPV is that most cases of HPV infection will regress independent of treatment. Persistence of the high-risk HPV types is necessary for the progression to HPV integration. Such progression occurs in a small percentage of patients. Therefore, a screening test with high sensitivity for HPV integration is desirable for early diagnosis and treatment.

One challenging sector for HPV testing is those women whose Pap test is read as ASCUS. The current recommendation for ASCUS is to have the patient, if 30 years old or older, tested for the presence or absence of HPV DNA. HPV can be detected by several types of tests. The most commonly used test in a clinical setting is the Digene Hc2 test, which is available in a standardized kit. This test involves the recognition of specific types of papillomavirus, and is recommended to replace or be used along with conventional cytological screening procedures.

One of the disadvantages to the Digene Hc2 test is that the test only identifies the presence of the viral DNA by hybridization procedures. Since in most patients HPV infection will be reversed without integration into the woman's genome, a positive Digene Hc2 test only lets the clinician know whether the virus is present or not. That is to say, the test does not indicate whether the virus has been actually integrated into the woman's genome. The corollary is that even if a clinician obtains a positive result from the Digene Hc2 test, a definitive answer as to the true presence of cancer cells cannot be provided. Additionally, the Digene Hc2 test is complex, time consuming, labor intensive and expensive.

To date, there is no treatment for an HPV infection. As such, a patient that has been diagnosed with an HPV infection can only be monitored with an increased frequency for the presence of cancer with Pap tests. Clearly, a test for HPV integration is desirable.

SUMMARY

An advanced cervical cancer screening method which involves screening cellular samples for lesions that can be treated at the earliest stages. In one embodiment, this is accomplished in a streamlined testing process where a single receiving structure can be used for both Pap staining and immunohistochemical testing, thereby improving sensitivity and specificity, as well as offering a low cost alternative to expensive HPV testing methods. The disclosed methods provide a molecular based process of detecting whether or not HPV has integrated into the woman's genome.

In one embodiment, a sample is taken by a cell collector that is preferably designed to collect cell clusters or clumps. In one example, the cell clusters or clumps are collected from the entire 360 degrees of the cervical cavity. In another example, the cell collector maintains the spatial orientation of the clusters or clumps when they are collected, so as to create a circular "cervical-map" representing the spatial relation of the cells to cervical anatomy, i.e., the endocervix, ectocervix and transformation zone relationships and the quadrant relationships.

Once the cells are collected by the clinician, they are transferred onto a receiving structure, for example a slide. In one embodiment, the slide is then Pap stained. In one example, if the results are positive, the same slide is then immunostained using one or more biomarkers.

The biomarkers used are antibodies to the HPV gene proteins. In one example, these proteins will only be detected if the HPV has integrated into the patient's genome. In this instance, the immunostaining allows one to determine whether HPV has integrated into the patient's genome. After the slide is stained, the slide is scanned to determine the degree of antibody recognition of the HPV early (E) gene products.

In yet another embodiment, after the cells are collected and transferred onto a receiving structure, for example a slide, the slide can be first immunostained using a biomarker, and scanned. It then can be decided which samples to Pap stain as a reflux test.

BRIEF DESCRIPTION OF THE DRAWINGS

FIGS. 1A-1C illustrate partial amino acid sequences of the E1 protein of the major high risk types of HPV. The underlined sequences indicate the areas of consensus from which the polypeptides were derived for producing the diagnostic antibodies in one embodiment of the disclosed methods.

FIG. 2 illustrates the amino acid sequences of the E4 protein of the major high risk types of HPV. The underlined sequences indicate the areas of consensus from which the polypeptides were derived for producing the diagnostic antibodies in one embodiment of the disclosed method.

FIG. 3 illustrates the amino acid sequences of the E5 protein of the major high risk types of HPV. The underlined sequences indicate the areas of consensus from which the polypeptides were derived for producing the diagnostic antibodies in one embodiment of the disclosed method.

FIGS. 4A and 4B illustrate the amino acid sequences of the E6 protein of the major high risk types of HPV. The underlined sequences indicate the areas of consensus from which the polypeptides were derived for producing the diagnostic antibodies in one embodiment of the disclosed method.

FIG. 5 illustrates the amino acid sequences of the E7 protein of the major high risk types of HPV. The underlined sequences indicate the areas of consensus from which the polypeptides were derived for producing the diagnostic antibodies in one embodiment of the disclosed method.

DETAILED DESCRIPTION

Overview

Figure 6:
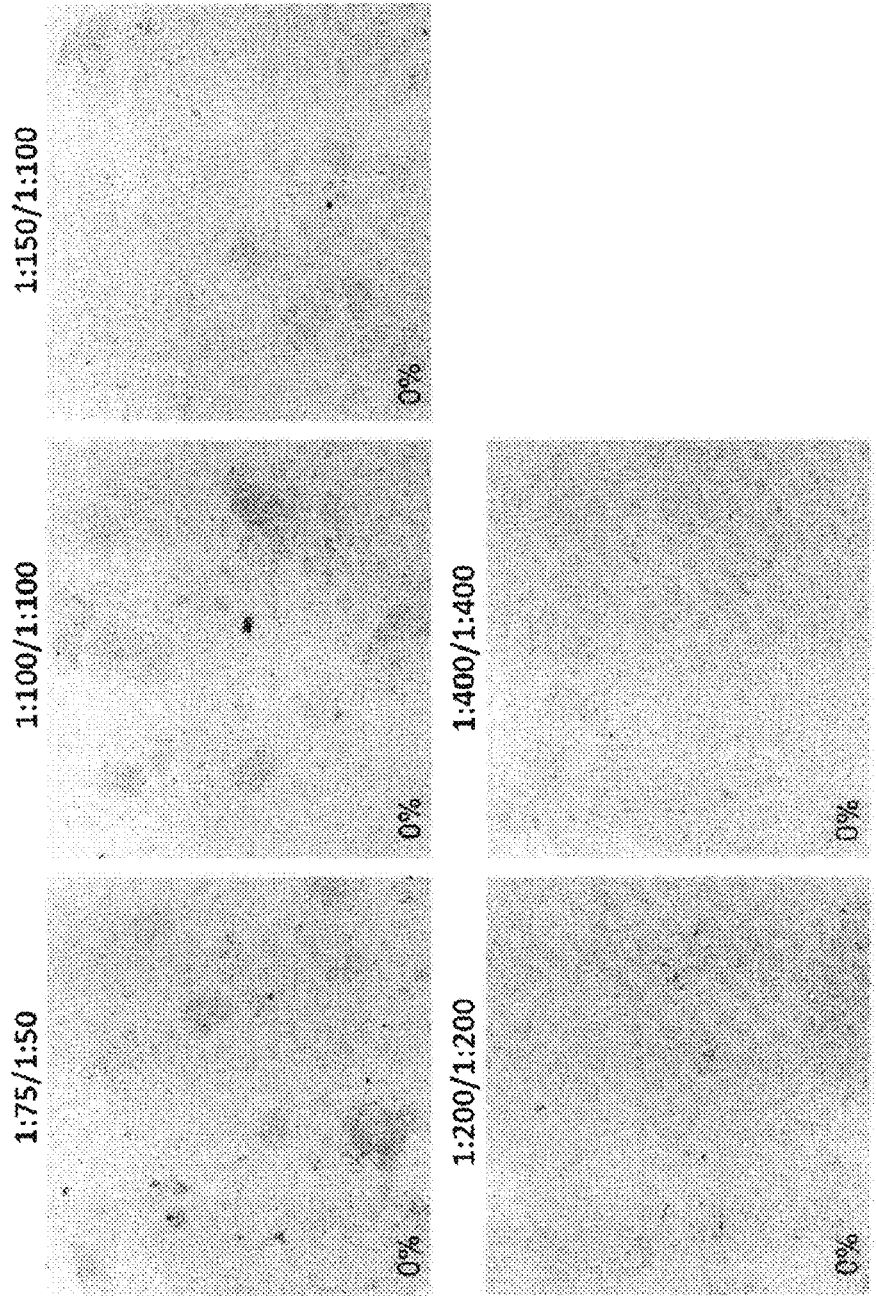
FIG. 6 illustrates cervical cells stained with HPV type 16 E6 and E7 antibodies. The stains show the cervical cells to be negative for HPV integration.

An advanced cervical cancer screening methods that provide a molecular based process of detecting HPV-integration. The disclosed methods allow for a streamlined approach of conducting a Pap test and immunohistochemical test on the same slide. The disclosed methods provides an inexpensive, highly sensitive, specific, and detailed test that is easy to evaluate and follow-up.

Generally, the method includes collecting clusters of cells using a collector that is designed to enhance the ability of the collector to pick up cluster of cells and to facilitate transfer of the collected clusters of cells onto a receiving structure, for example a slide. In one example, the clusters of cells are transferred from the collector to the slide using a transfer station in such a way as to retain the spatial orientation that existed between the cells in the clusters prior to sampling.

In one embodiment, a lab performs a Pap stain on the slide. The type of Pap staining method utilized is not particularly limited, and may be a Pap staining method that is conventionally utilized.

In one example, the method involves following standard clinical guidelines if the test is negative. If the test is positive, then the slide is stained using an antibody for an HPV-integration marker conjugated with a fluorescent or calorimetric tag. In one instance, the HPV-integration marker used is an HPV gene product (protein). The type of HPV gene product utilized is not particularly limited, and includes E1, E4, E5, E6 and E7 proteins. The staining method and the marker used are not particularly limited, so long as an immunohistochemical localization of an HPV-integration marker can be achieved.

The slide is then scanned. The scanner used is not particularly limited, and may be an automated or manual scanner or automated or manual microscope. The scanner is used for scanning fluorescent or color signals and thereby recognizing whether the HPV gene product is present in the cervical cells.

Collection

A collector is used for collecting cells and cluster of cells. The collector can be any form of collector that is capable of collecting cells and cell clusters. Examples of suitable collectors are described in published U.S. patent applications US 2006/0189893 and US 2006/0161076, which are incorporated by reference herein in their entirety. Among other details of a collector that can be used, these two publications describe a combination of the material of the collector, the texture of the collection surface of the collector, and the use of expansion and rotation of the collector during collection facilitate the collection of the clusters of cells. The collector obtains cell clusters from the endo- and ecto-cervical regions of the cervix.

Receiving Structure

Where a receiving structure is used, the receiving structure utilized is not particularly limited. Examples of a suitable receiving structure include a slide, a Petri dish, a membrane, and other structures to which cells and cell clusters may be transferred for subsequent analysis. In one example, the receiving structure has greater adhesiveness than the surface of the collector containing the cells and cell clusters to enhance the transfer of cell clusters from the collector to the receiving structure. When the receiving structure is a slide, the slide can be pre-treated with a coating that results in the greater adhesiveness. An example of a suitable slide has a poly-L-lysine based coating that helps cells adhere to the slide.

In another embodiment, a receiving structure is not utilized. In this instance, the cervical cells are collected in suspension in fixative and then the immunologic testing is performed directly on the suspended cells with no intervening receiving structure.

Pap Test

Once the clusters of cells are transferred onto an appropriate receiving structure, for example a slide, a conventional Pap test is conducted. This test involves staining the slide according to the Papanicolaou method and evaluated according to the Bethesda system. Cytology is considered negative if the cells appear normal, or show atrophy, metaplasia, or inflammatory changes. A positive Pap smear is defined as ASCUS or worse.

In another embodiment, the disclosed method involves conducting a Pap test as a reflex test after conducting a HPV integration test by immunostaining.

Immunostaining

In one example, once the Pap test is confirmed to be positive, immunostaining is performed with one or more HPV-integration markers. The immunostaining method utilized is not particularly limited. For example, either direct or indirect immunostaining may be performed. In the case where direct immunostaining is performed, the detection system is covalently linked or conjugated directly to the primary antibody. The detection system utilized may be either fluorescence labeling or enzyme substrate labeling. In the case where a fluorescent marker is used, an exemplary protocol involves washing the slide, blocking with a blocking solution, staining with an HPV-integration marker specific antibody conjugated with a fluorescent label, and then washing the slide. The slide is then read manually with a fluorescent microscope or by an automated fluorescent scanner. The scanner detects and localizes the HPV-integration markers in cells that have had HPV integrated into the DNA. Abundance of HPV-integration marker expression is also determined by quantitative assessment of the signal.

In the case where an enzyme-substrate labeling is used, the enzyme must have a substrate system that generates a product that can be visualized and has minimal diffusion from the site of production. The histochemical enzyme utilized is not particularly limited, and may include, for example, anyone of the following: horseradish peroxidase, alkaline phosphatase, glucose oxidase or beta-galactosidase. An exemplary protocol for this type of system involves blocking with a blocking solution, incubating with an HPV-integration marker specific antibody conjugated with a histochemical enzyme, washing the slide and then treating with a substrate. The substrate may be a chromogen substrate, and may be any one of the following: diaminobenzidine (DAB), aminoethylcarbazole (AEC), alphanaphthol pyronin, 4-chloro-1-napthol, paraphenylenediamine pyrocatechol, fast red TR, fast blue BB, BCIPINBT, tetrazolium blue or BCl. The slide is then read by an automated calorimetric scanner and the brightness of the signal is quantitatively assessed. As an alternative, a standard microscope is used to review the slide and identify both the presence of the molecular marker and any morphological changes to the cells.

In the case where indirect staining is employed, an exemplary protocol involves incubation with an unlabled primary antibody specific to an HPV-integration marker, washing, incubation with a secondary antibody conjugated with a histochemical enzyme label, followed by washing and detection.

Quantitative Assessment of Immunohistochemical Stains

The method for quantitatively assessing the abundance of marker expression is not particularly limited. In the case of immunofluorescent staining, the scanned histological image can be evaluated with an image analysis software, for example, Analyze. The software allows one to determine the density of the signal, and calculate the brightness-area-product (BAP). The BAP can provide a means to objectively compare the intensity of staining in identical anatomical regions exposed to the same staining regimen. BAP can be calculated using the following formula:

(Mean pixel brightness in range−Minimum brightness in range)×(Number of pixels in range).

In the case where a calorimetric tag is used, the scanned image is imported into an S-VHS port of a computer using a one-chip CCD red-green-blue (RGB) color video camera and a standard diagnostic microscope. The software used to evaluate the color signal can be, for example, Photoshop, but is not particularly limited. If Photoshop is used, the signal is quantified, for example, using the Histogram command to measure the tonal distribution as the basis for automated image manipulation. This feature allows spatial information to be obtained for a specific substrate used, for example, chromagen, and can be expressed as a percentage of the entire image or in $\mu m^2$.

In yet another embodiment, the calorimetric tag may be quantified by counting the percent of cells that are positive.

HPV-Integration Marker

In one embodiment, the antibody utilized in the disclosed method is specific to an HPV-integration marker. The term "specific antibody against an HPV integration marker" herein means a specific antibody against an epitope of a protein product of an HPV gene, for example, an epitope of a gene product resulting from HPV integration including, but not limited to E1, E4, E5, E6 and/or E7. The term "epitope" herein refers to a site on an antigen to which B and/or T cells respond. The antigen may be a polypeptide or a protein product. The site may be a polypeptide. In one example, an epitope may be the antigen, and may refer to a polypeptide of an HPV-integration marker.

Although antibodies are most often sought that are specific to only one protein or polypeptide, it is the purpose of the present inventors to utilize antibodies that will recognize a protein family coming from any of the high risk HPV types. To that end, the present inventors have chosen areas of consensus among the high risk type HPVs in the respective proteins of interest. FIGS. 1A-1C show highly conserved areas of the E1 protein. FIG. 2 shows highly conserved areas of the E4 protein. FIG. 3 shows highly conserved areas of the E5 protein. FIGS. 4A and 4B show highly conserved areas of the E6 protein. FIG. 5 show highly conserved areas of the E7 protein.

Preparation of Antibodies

Antibodies can be raised in any suitable animal, for example, mice or rabbits, using standard immunization techniques well documented in the prior art by injection and then booster injections of antigen mixtures. For preparation of monoclonal panels, the immunized animals are sacrificed and spleen cells harvested for immortalization to obtain cells capable of producing the desired antibody. The supernatants from these cells are screened with the injected polypeptide as a first test of the presence of the antibody of interest.

EXAMPLE 1

In one example, antibodies were raised against polypeptides utilizing the HPV E1 gene. Specific examples of the polypeptides used to raise the antibodies are provided as follows:

At position 202 of HPV type 16: SNAKAMLAKFKELYGC (SEQ ID NO: 1) and at position 208 of HPV type 18: NNKQGAMLAVFKDTYGC (SEQ ID NO: 2); and at position 293 of HPV type 16: LSKLLCVSPMC(ACM)MMIEPPKLR (SEQ ID NO: 3) and at position 301 of HPV type 18: LSTLLHVPETAMLIEPPKLR (SEQ ID NO: 4) and at position 286 of HPV types 33, 52 and 58: LSSLLNIPQSQMLIQPPKLR (SEQ ID NO: 5); and at position 606 of HPV type 16: DKNWKSFFSRTWC (SEQ ID NO: 6) and at position 613 of HPV type 18: DKNWKCFFERTWC (SEQ ID NO: 7) and at position 587 of HPV types 26, 51, 66, and 73: NENWKAFFTKTWC (SEQ ID NO: 8); and at position 640 of HPV type 16: CVSGQNTNTL (SEQ ID NO: 9) and at position 648 of HPV type 18: CLRAGQNHRPL (SEQ ID NO: 10) and at position 620 of HPV types 26, 31, 33, 39, 45, 51, 52, 58, and 59: CSTGENIRSI (SEQ ID NO: 11).

In another example, antibodies were raised against polypeptides utilizing the HPV E4 gene. Specific examples of the polypeptides used to raise the antibodies are provided as follows:

At position 44 of HPV type 16: RRLSSDQD (SEQ ID NO: 12), at position 79 of HPV type 16: LTAHQTK (SEQ ID NO: 13), and at position 85 of HPV type 16: DGLTVIVTL (SEQ ID NO: 14).

In another example, antibodies were raised against polypeptides utilizing the HPV E5 gene. Specific examples of the polypeptides used to raise the antibodies are provided as follows:

At position 5 of HPV types 52, 58 and 33: VFC(ACM)FILFLC(ACM)LC (SEQ ID NO: 15) and at position 15 of HPV type 35: LC(ACM)FC(ACM)VLLC(ACM)LCL (SEQ ID NO: 16) and, at position 30 of HPV type 18: AYAWVLVFVYIVV (SEQ ID NO: 17) and, at position 31 of HPV type 51 and 69: PLLLSQYVFAAHLLLII (SEQ ID NO: 18) and, at position 37 of HPV type 16: STYTSLIOLV (SEQ ID NO: 19) and, at position 51 of HPV type 73: FFLYVLVFYIF (SEQ ID NO: 20).

In another example, antibodies were raised against polypeptides utilizing the HPV E6 gene. Specific examples of the polypeptides used to raise the antibodies are provided as follows:

At position 126 of HPV type 16: LDKKRRFHNI (SEQ ID NO: 21) and LNEKKRFHNI (SEQ ID NO: 22) and LDKKQRFHNI (SEQ ID NO: 23), at position 129 of HPV type 16: KQRFHNIRGRWTGRC (SEQ ID NO: 24) and KRRFHNIAGRYTGQC (SEQ ID NO: 25) and NKRFHNIRGRWTGRC (SEQ ID NO: 26).

In another example, antibodies were raised against polypeptides utilizing the HPV E7 gene. Specific examples of the polypeptides used to raise the antibodies are provided as follows:

At position 29 of HPV type 16: DSSEENDEID (SEQ ID NO: 27) and, at position 41 of HPV type 16: PAGGA (SEQ ID NO: 28) and, at position 89 of HPV type 16: VCPIC (SEQ ID NO: 29).

The above polypeptides were designed so that antibodies to them could be used in combination to recognize all of the high risk types of HPV in a single assay mixture.

EXAMPLE 2

One example of the disclosed method includes fixing the cervical cells, depositing the cells on a slide by cyto-centrifuge for 2 minutes at 1000 RPM at room temperature, incubation of the slide for 30 minutes in 0.01M Citrate buffer, pH 6.0, washing the slide in TBST (Tris-buffered saline containing Tween 20 for 5 minutes, incubating the slide for 10 minutes with normal fetal calf serum blocking buffer (10% FCS in TBST), incubation with the primary monoclonal mouse antibody in diluents buffer (1 FCS in TBST) for one hour at a dilution of 1:50, 1:75 or 1:100 (optimal dilution varies for each antibody), washing the slide in TBST for 5 minutes, incubation with a secondary rabbit-anti-mouse antibody conjugated with HRP (horse radish peroxidase), and then incubation for 10 minutes with the DAB (diamino benzidene chromagen) substrate for the HRP enzyme, rinsing the slide in distilled water for 1 minute, and after drying, adding 1 drop of DAPI nuclear stain. This produces a brown color in the cells which contain the antigen with which the primary antibody has reacted. 250 cells then can be counted with a bright field microscope to determine the percentage of cells that are positively stained.

Figure 7:
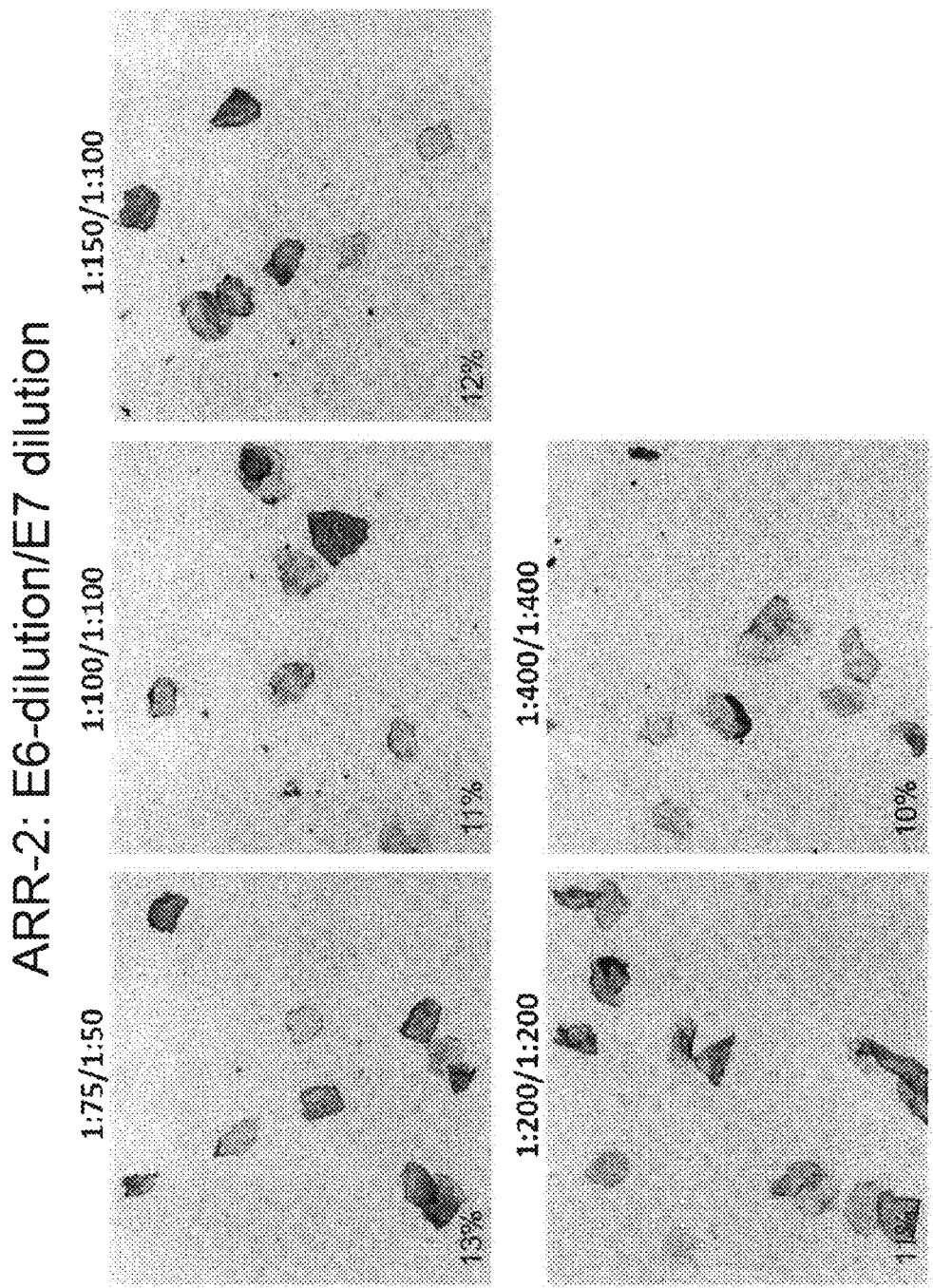
FIG. 7 illustrates cervical cells stained with HPV type 16 E6 and E7 antibodies. The stains show the cervical cells to be positive for HPV integration.
Figure 8:
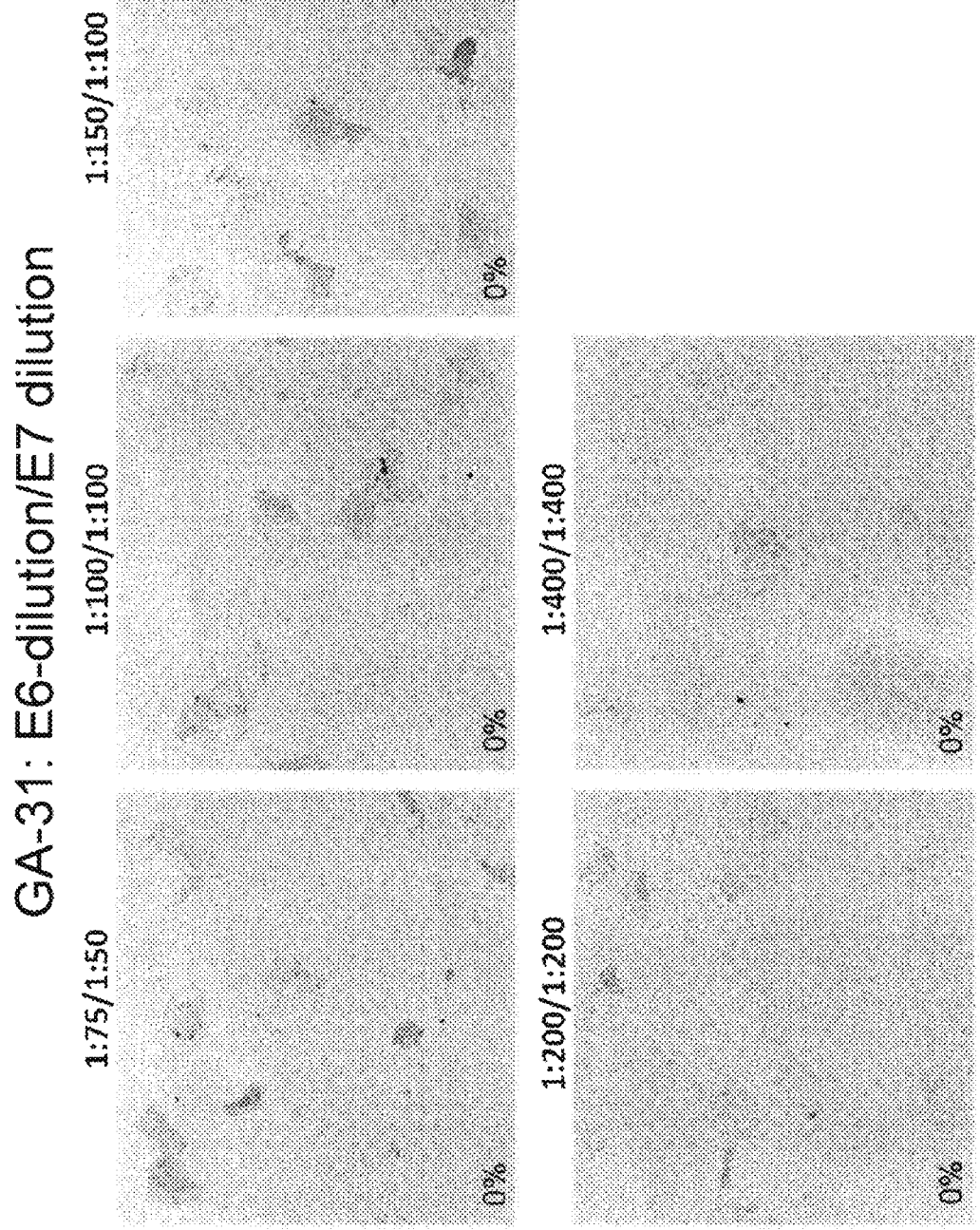
FIG. 8 illustrates cervical cells stained with HPV type 16 E6 and E7 antibodies. The stains show the cervical cells to be negative for HPV integration.
Figure 9:
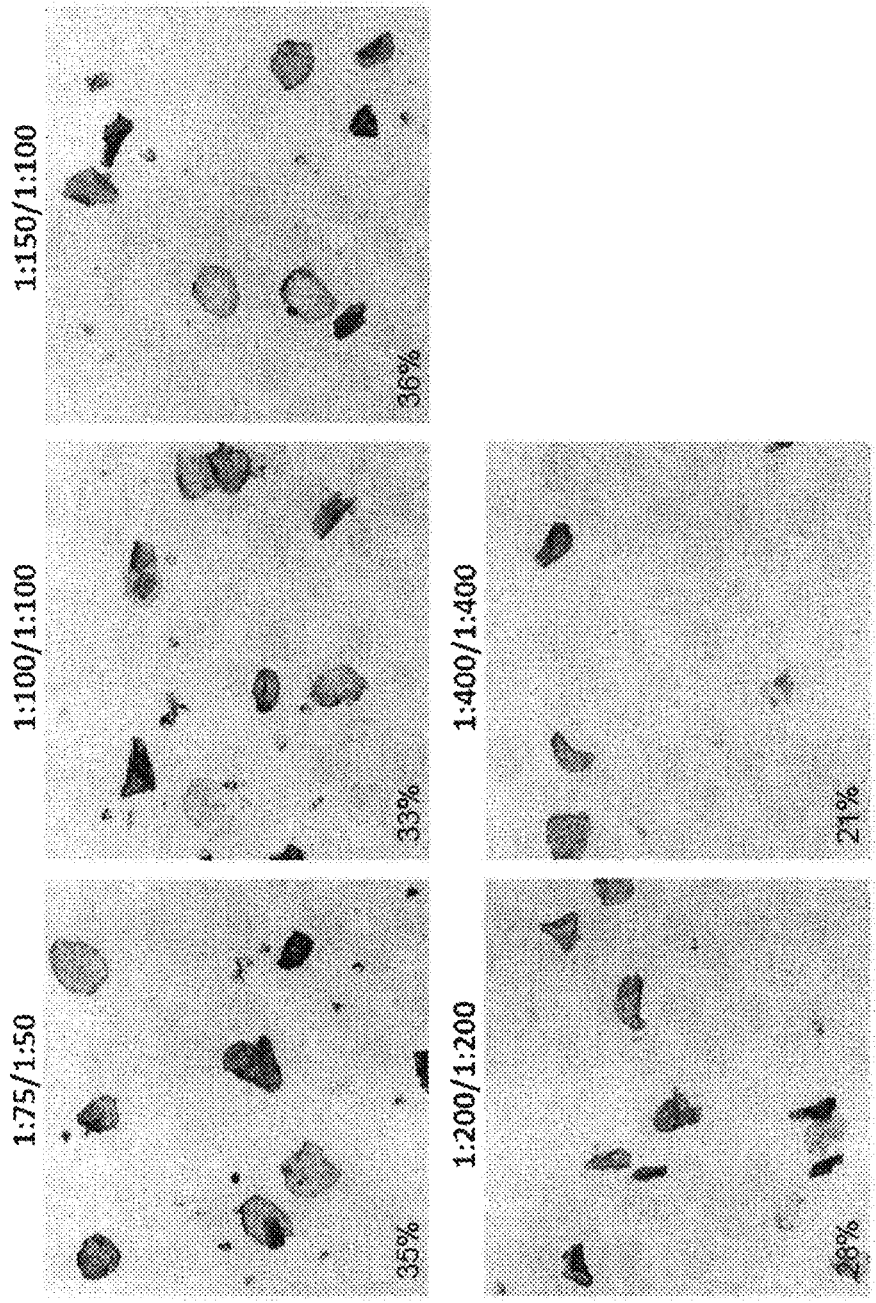
FIG. 9 illustrates cervical cells stained with HPV type 16 E-6 and E-7 antibodies. The stains show the cervical cells to be positive for HPV integration.

Using this methodology on a series of clinical samples taken from patients undergoing colposcopy and accordingly more likely to have HPV integration and a cervical lesion, the present inventors have found the following results shown in the table below and FIGS. 6-9.

| SAMPLE I.D. | % Positive with HPV16 E6 Antibody | % Positive with HPV16 E7 Antibody | % Positive with both antibodies |
|---|---|---|---|
| ARR 2 | 12 | 18 | 17 |
| ARR 14 | 0 | 2 | 2 |
| ARR 16 | 0 | 0 | 0 |
| ARR 18 | 7 | 4 | 4 |
| ARR 19 | 0 | 0 | 0 |
| ARR 22 | 0 | 1 | 0 |
| ARR 24 | 0 | 3 | 0 |
| GA 1 | 0 | 0 | 0 |
| GA 3 | 34 | 51 | 38 |
| GA 9 | 0 | 0 | 0 |
| GA 12 | 0 | 0 | 0 |
| GA 19 | 8 | 6 | 5 |
| GA 20 | 0 | 1 | 2 |
| GA 21 | 0 | 2 | 1 |
| GA 24 | 0 | 3 | 0 |
| GA 25 | 2 | 3 | 2 |
| GA 26 | 0 | 0 | 0 |
| GA 31 | 0 | 1 | 1 |
| GA 33 | 19 | 25 | 21 |
| WHR 2 | 0 | 1 | 1 |

The results as shown above and in FIGS. 6-9 suggest that for the individual patient it is clear which ones have an integrated HPV and which ones do not. They also suggest that for E6 and E7 antibodies, the information from using them singly is the same as when using them in combination. Lastly, it is noteworthy that 5/20 (25%) of these patients were positive for HPV type 16 integration, but they come from a subset of patients already known to have abnormal Pap tests.

Implementation Models

The advanced cervical cancer screening methods can be utilized by any size or structured laboratories. Preferably, the methods are utilized by labs or caregivers that already perform Pap testing.

The advanced cervical cancer screening methods deliver a unique collection process that provides value added services to the screening of cervical cancer for improved management of patients. The methods involve the analysis of a cytological sample by both a Pap test and immunohistochemical staining in a streamlined approach, thereby allowing the efficient identification of not only true and false positives, but also true and false negatives. The present methods provide a more definitive and detailed results as compared to conventional methods to the physician or surgeon with a single cell collection process. The advantages include: improved positive and negative predictive value since the marker indicates when viral integration into the woman's genome has occurred; proprietary collection process that allows for improved patient comfort during cell collection; a low cost solution; collection of a surplus of cells that exhibit high uniformity, quality and integrity, as the volume of cells allows for multiple screening tests to be performed from a single sample collection; and a streamlined testing process, where a single slide can be used for both Pap staining and immunocytochemical testing.

The present methods provide benefits to a lab, as the methods provide a low cost alternative before going to expensive type specific HR-HPV testing methods, aids elimination of false positives and proper classification of ASCUS samples by providing a test method with improved sensitivity and specificity, provides entry to the cervical cancer molecular diagnostic market and expands the portfolio of complex diagnostic services to current and new customers.

It is also clear that the above methods could be utilized as a primary screening test for cervical cancer without the Pap test being done.

While the invention has been described in conjunction with exemplary embodiments, it will be obvious to one skilled in the art that other refinements of the present invention may be made with the present invention within the purview and scope of the present invention which resides in the following claims. The disclosed details are not to be taken as limitations on the invention.

---

What is claimed is:

1. A method of screening for human papilloma virus (HPV) integration, the method comprising:

(a) applying an antibody specific to an HPV integration marker to cells and clusters of cells, the cells and clusters of cells being part of a sample of cells and clusters of cells taken from a cervix, and (b) manually or by automated means reading the information obtained from analyzing the cells and clusters of cells, wherein the antibody is raised against at least one polypeptide selected from the group consisting of SEQ ID NO: 21, SEQ ID NO: 22, SEQ ID NO: 23, SEQ ID NO: 25, SEQ ID NO: 26, SEQ ID NO: 27 and SEQ ID NO: 28.

* * * * *

SEQUENCE LISTING

```
<160> NUMBER OF SEQ ID NOS: 122

<210> SEQ ID NO 1
<211> LENGTH: 16
<212> TYPE: PRT
<213> ORGANISM: Human papillomavirus type 16

<400> SEQUENCE: 1

Ser Asn Ala Lys Ala Met Leu Ala Lys Phe Lys Glu Leu Tyr Gly Cys
1               5                   10                  15

<210> SEQ ID NO 2
<211> LENGTH: 17
<212> TYPE: PRT
<213> ORGANISM: Human papillomavirus type 16

<400> SEQUENCE: 2

Asn Asn Lys Gln Gly Ala Met Leu Ala Val Phe Lys Asp Thr Tyr Gly
1               5                   10                  15

Cys

<210> SEQ ID NO 3
<211> LENGTH: 23
<212> TYPE: PRT
<213> ORGANISM: Human papillomavirus type 16

<400> SEQUENCE: 3

Leu Ser Lys Leu Leu Cys Val Ser Pro Met Cys Ala Cys Met Met Met
1               5                   10                  15

Ile Glu Pro Pro Lys Leu Arg
            20

<210> SEQ ID NO 4
<211> LENGTH: 20
<212> TYPE: PRT
<213> ORGANISM: Human papillomavirus type 16

<400> SEQUENCE: 4
```

```
Leu Ser Thr Leu Leu His Val Pro Glu Thr Ala Met Leu Ile Glu Pro
1               5                   10                  15

Pro Lys Leu Arg
            20

<210> SEQ ID NO 5
<211> LENGTH: 20
<212> TYPE: PRT
<213> ORGANISM: Human papillomavirus type 16

<400> SEQUENCE: 5

Leu Ser Ser Leu Leu Asn Ile Pro Gln Ser Gln Met Leu Ile Gln Pro
1               5                   10                  15

Pro Lys Leu Arg
            20

<210> SEQ ID NO 6
<211> LENGTH: 13
<212> TYPE: PRT
<213> ORGANISM: Human papillomavirus type 16

<400> SEQUENCE: 6

Asp Lys Asn Trp Lys Ser Phe Phe Ser Arg Thr Trp Cys
1               5                   10

<210> SEQ ID NO 7
<211> LENGTH: 13
<212> TYPE: PRT
<213> ORGANISM: Human papillomavirus type 16

<400> SEQUENCE: 7

Asp Lys Asn Trp Lys Cys Phe Phe Glu Arg Thr Trp Cys
1               5                   10

<210> SEQ ID NO 8
<211> LENGTH: 13
<212> TYPE: PRT
<213> ORGANISM: Human papillomavirus type 16

<400> SEQUENCE: 8

Asn Glu Asn Trp Lys Ala Phe Phe Thr Lys Thr Trp Cys
1               5                   10

<210> SEQ ID NO 9
<211> LENGTH: 10
<212> TYPE: PRT
<213> ORGANISM: Human papillomavirus type 16

<400> SEQUENCE: 9

Cys Val Ser Gly Gln Asn Thr Asn Thr Leu
1               5                   10

<210> SEQ ID NO 10
<211> LENGTH: 11
<212> TYPE: PRT
<213> ORGANISM: Human papillomavirus type 16

<400> SEQUENCE: 10

Cys Leu Arg Ala Gly Gln Asn His Arg Pro Leu
1               5                   10

<210> SEQ ID NO 11
<211> LENGTH: 10
<212> TYPE: PRT
```

-continued

<213> ORGANISM: Human papillomavirus type 16

<400> SEQUENCE: 11

Cys Ser Thr Gly Glu Asn Ile Arg Ser Ile
1               5                   10

<210> SEQ ID NO 12
<211> LENGTH: 8
<212> TYPE: PRT
<213> ORGANISM: Human papillomavirus type 16

<400> SEQUENCE: 12

Arg Arg Leu Ser Ser Asp Gln Asp
1               5

<210> SEQ ID NO 13
<211> LENGTH: 7
<212> TYPE: PRT
<213> ORGANISM: Human papillomavirus type 16

<400> SEQUENCE: 13

Leu Thr Ala His Gln Thr Lys
1               5

<210> SEQ ID NO 14
<211> LENGTH: 9
<212> TYPE: PRT
<213> ORGANISM: Human papillomavirus type 16

<400> SEQUENCE: 14

Asp Gly Leu Thr Val Ile Val Thr Leu
1               5

<210> SEQ ID NO 15
<211> LENGTH: 11
<212> TYPE: PRT
<213> ORGANISM: Human papillomavirus type 52

<400> SEQUENCE: 15

Val Phe Cys Phe Ile Leu Leu Met Val Phe Cys
1               5                   10

<210> SEQ ID NO 16
<211> LENGTH: 11
<212> TYPE: PRT
<213> ORGANISM: Human papillomavirus type 35

<400> SEQUENCE: 16

Leu Cys Leu Cys Val Cys Leu Val Leu Cys Cys
1               5                   10

<210> SEQ ID NO 17
<211> LENGTH: 13
<212> TYPE: PRT
<213> ORGANISM: Human papillomavirus type 18

<400> SEQUENCE: 17

Ala Tyr Ala Trp Val Leu Val Phe Val Tyr Ile Val Val
1               5                   10

<210> SEQ ID NO 18
<211> LENGTH: 16
<212> TYPE: PRT
<213> ORGANISM: Human papillomavirus type 51

```
<400> SEQUENCE: 18

Pro Leu Leu Leu Ser Gln Tyr Val Phe Ala Ala Ala Leu Leu Leu Ile
1               5                   10                  15

<210> SEQ ID NO 19
<211> LENGTH: 10
<212> TYPE: PRT
<213> ORGANISM: Human papillomavirus type 16

<400> SEQUENCE: 19

Ser Thr Tyr Thr Ser Leu Ile Ile Leu Val
1               5                   10

<210> SEQ ID NO 20
<211> LENGTH: 11
<212> TYPE: PRT
<213> ORGANISM: Human papillomavirus type 73

<400> SEQUENCE: 20

Phe Phe Leu Tyr Val Leu Val Phe Tyr Ile Pro
1               5                   10

<210> SEQ ID NO 21
<211> LENGTH: 10
<212> TYPE: PRT
<213> ORGANISM: Human papillomavirus type 16

<400> SEQUENCE: 21

Leu Asp Lys Lys Gln Arg Phe His Asn Ile
1               5                   10

<210> SEQ ID NO 22
<211> LENGTH: 10
<212> TYPE: PRT
<213> ORGANISM: Human papillomavirus type 18

<400> SEQUENCE: 22

Leu Asn Glu Lys Arg Arg Phe His Asn Ile
1               5                   10

<210> SEQ ID NO 23
<211> LENGTH: 10
<212> TYPE: PRT
<213> ORGANISM: Human papillomavirus type 16

<400> SEQUENCE: 23

Leu Asp Lys Lys Arg Arg Phe His Asn Ile
1               5                   10

<210> SEQ ID NO 24
<211> LENGTH: 13
<212> TYPE: PRT
<213> ORGANISM: Human papillomavirus type 16

<400> SEQUENCE: 24

Arg Phe His Asn Ile Arg Gly Arg Trp Thr Gly Arg Cys
1               5                   10

<210> SEQ ID NO 25
<211> LENGTH: 15
<212> TYPE: PRT
<213> ORGANISM: Human papillomavirus type 18

<400> SEQUENCE: 25
```

-continued

```
Lys Arg Arg Phe His Asn Ile Ala Gly Arg Tyr Thr Gly Gln Cys
1               5                   10                  15

<210> SEQ ID NO 26
<211> LENGTH: 15
<212> TYPE: PRT
<213> ORGANISM: Human papillomavirus type 52

<400> SEQUENCE: 26

Asn Lys Arg Phe His Asn Ile Arg Gly Arg Trp Thr Gly Arg Cys
1               5                   10                  15

<210> SEQ ID NO 27
<211> LENGTH: 10
<212> TYPE: PRT
<213> ORGANISM: Human papillomavirus type 16

<400> SEQUENCE: 27

Asp Ser Ser Glu Glu Asn Asp Glu Ile Asp
1               5                   10

<210> SEQ ID NO 28
<211> LENGTH: 5
<212> TYPE: PRT
<213> ORGANISM: Human papillomavirus type 16

<400> SEQUENCE: 28

Pro Ala Gly Gly Ala
1               5

<210> SEQ ID NO 29
<211> LENGTH: 5
<212> TYPE: PRT
<213> ORGANISM: Human papillomavirus type 16

<400> SEQUENCE: 29

Val Cys Pro Ile Cys
1               5

<210> SEQ ID NO 30
<211> LENGTH: 30
<212> TYPE: PRT
<213> ORGANISM: Human papillomavirus type 16

<400> SEQUENCE: 30

Leu Lys Thr Ser Asn Ala Lys Ala Ala Met Leu Ala Lys Phe Lys Glu
1               5                   10                  15

Leu Tyr Gly Val Ser Phe Ser Glu Leu Val Arg Pro Phe Lys
            20                  25                  30

<210> SEQ ID NO 31
<211> LENGTH: 30
<212> TYPE: PRT
<213> ORGANISM: Human papillomavirus type 16

<400> SEQUENCE: 31

Glu Thr Ile Glu Lys Leu Leu Ser Lys Leu Leu Cys Val Ser Pro Met
1               5                   10                  15

Cys Met Met Ile Glu Pro Pro Lys Leu Arg Ser Thr Ala Ala
            20                  25                  30

<210> SEQ ID NO 32
<211> LENGTH: 30
<212> TYPE: PRT
```

<213> ORGANISM: Human papillomavirus type 18

<400> SEQUENCE: 32

Leu Lys Val Asn Asn Lys Gln Gly Ala Met Leu Ala Val Phe Lys Asp
1               5                   10                  15

Thr Tyr Gly Leu Ser Phe Thr Asp Leu Val Arg Asn Phe Lys
            20                  25                  30

<210> SEQ ID NO 33
<211> LENGTH: 30
<212> TYPE: PRT
<213> ORGANISM: Human papillomavirus type 18

<400> SEQUENCE: 33

Leu Thr Val Ala Lys Gly Leu Ser Thr Leu Leu His Val Pro Glu Thr
1               5                   10                  15

Cys Met Leu Ile Gln Pro Pro Lys Leu Arg Ser Ser Val Ala
            20                  25                  30

<210> SEQ ID NO 34
<211> LENGTH: 30
<212> TYPE: PRT
<213> ORGANISM: Human papillomavirus type 26

<400> SEQUENCE: 34

Leu Lys Cys Ser Asn Val Lys Ala Ala Leu Leu Ser Lys Phe Lys Thr
1               5                   10                  15

Val Tyr Gly Val Ser Phe Ala Glu Leu Val Arg Val Phe Lys
            20                  25                  30

<210> SEQ ID NO 35
<211> LENGTH: 30
<212> TYPE: PRT
<213> ORGANISM: Human papillomavirus type 26

<400> SEQUENCE: 35

Thr Thr Ile Lys Asn Cys Leu Cys Met Leu Asn Val Pro Glu Thr
1               5                   10                  15

Gln Leu Leu Ile Glu Pro Pro Lys Leu Arg Ser Thr Ala Val
            20                  25                  30

<210> SEQ ID NO 36
<211> LENGTH: 30
<212> TYPE: PRT
<213> ORGANISM: Human papillomavirus type 31

<400> SEQUENCE: 36

Leu Lys Thr Ser Asn Gly Lys Ala Ala Met Leu Gly Lys Phe Lys Glu
1               5                   10                  15

Leu Tyr Gly Val Ser Phe Met Glu Leu Ile Arg Pro Phe Gln
            20                  25                  30

<210> SEQ ID NO 37
<211> LENGTH: 30
<212> TYPE: PRT
<213> ORGANISM: Human papillomavirus type 31

<400> SEQUENCE: 37

Ile Thr Ile Glu Lys Leu Leu Glu Lys Leu Leu Cys Ile Ser Thr Asn
1               5                   10                  15

Cys Met Leu Ile Gln Pro Pro Lys Leu Arg Ser Thr Ala Ala
            20                  25                  30

```
<210> SEQ ID NO 38
<211> LENGTH: 30
<212> TYPE: PRT
<213> ORGANISM: Human papillomavirus type 33

<400> SEQUENCE: 38

Leu His Ser Ser Asn Thr Lys Ala Asn Ile Leu Tyr Lys Phe Lys Glu
1               5                   10                  15

Ala Tyr Gly Ile Ser Phe Met Glu Leu Val Arg Pro Phe Lys
            20                  25                  30

<210> SEQ ID NO 39
<211> LENGTH: 30
<212> TYPE: PRT
<213> ORGANISM: Human papillomavirus type 33

<400> SEQUENCE: 39

Leu Thr Val Ala Lys Leu Met Ser Asn Leu Leu Ser Ile Pro Glu Thr
1               5                   10                  15

Cys Met Val Ile Glu Pro Pro Lys Leu Arg Ser Gln Thr Cys
            20                  25                  30

<210> SEQ ID NO 40
<211> LENGTH: 30
<212> TYPE: PRT
<213> ORGANISM: Human papillomavirus type 35

<400> SEQUENCE: 40

Leu Lys Cys Ser Asn Ala Asn Ala Ala Met Leu Ala Lys Phe Lys Glu
1               5                   10                  15

Leu Phe Gly Ile Ser Phe Thr Glu Leu Ile Arg Pro Phe Lys
            20                  25                  30

<210> SEQ ID NO 41
<211> LENGTH: 30
<212> TYPE: PRT
<213> ORGANISM: Human papillomavirus type 35

<400> SEQUENCE: 41

Thr Thr Ile Glu Lys Leu Leu Ser Lys Leu Leu Cys Ile Ser Ala Ala
1               5                   10                  15

Ser Met Leu Ile Gln Pro Pro Lys Leu Arg Ser Thr Pro Ala
            20                  25                  30

<210> SEQ ID NO 42
<211> LENGTH: 30
<212> TYPE: PRT
<213> ORGANISM: Human papillomavirus type 39

<400> SEQUENCE: 42

Leu Gln Ser Asn Asn Lys Lys Ala Ala Met Leu Thr Gln Phe Lys Glu
1               5                   10                  15

Thr Tyr Gly Leu Ser Phe Thr Asp Leu Val Arg Thr Phe Lys
            20                  25                  30

<210> SEQ ID NO 43
<211> LENGTH: 30
<212> TYPE: PRT
<213> ORGANISM: Human papillomavirus type 39

<400> SEQUENCE: 43
```

```
Val Thr Val Gly Lys Gly Leu Ser Thr Leu Leu His Val Pro Glu Ser
1               5                   10                  15

Cys Met Leu Leu Glu Pro Pro Lys Leu Arg Ser Pro Val Ala
            20                  25                  30

<210> SEQ ID NO 44
<211> LENGTH: 30
<212> TYPE: PRT
<213> ORGANISM: Human papillomavirus type 45

<400> SEQUENCE: 44

Leu Gln Ala Ser Asn Lys Lys Ala Ala Met Leu Ala Val Phe Lys Asp
1               5                   10                  15

Ile Tyr Gly Leu Ser Phe Thr Asp Leu Val Arg Asn Phe Lys
            20                  25                  30

<210> SEQ ID NO 45
<211> LENGTH: 30
<212> TYPE: PRT
<213> ORGANISM: Human papillomavirus type 45

<400> SEQUENCE: 45

Leu Thr Val Ala Lys Gly Leu Ser Thr Leu Leu His Val Pro Glu Thr
1               5                   10                  15

Cys Met Leu Ile Glu Pro Pro Lys Leu Arg Ser Ser Val Ala
            20                  25                  30

<210> SEQ ID NO 46
<211> LENGTH: 30
<212> TYPE: PRT
<213> ORGANISM: Human papillomavirus type 51

<400> SEQUENCE: 46

Leu Lys Ser Ser Asn Ala Lys Ala Thr Leu Met Ala Lys Phe Lys Glu
1               5                   10                  15

Leu Tyr Gly Ile Ser Tyr Asn Glu Leu Val Arg Val Phe Lys
            20                  25                  30

<210> SEQ ID NO 47
<211> LENGTH: 30
<212> TYPE: PRT
<213> ORGANISM: Human papillomavirus type 51

<400> SEQUENCE: 47

Thr Thr Ile Ala Lys Cys Leu Ser Thr Leu Val Asn Ile Pro Gln Ser
1               5                   10                  15

Gln Met Phe Ile Glu Pro Pro Lys Leu Arg Ser Thr Pro Val
            20                  25                  30

<210> SEQ ID NO 48
<211> LENGTH: 30
<212> TYPE: PRT
<213> ORGANISM: Human papillomavirus type 52

<400> SEQUENCE: 48

Met Cys Glu Asn Ser Ile Lys Thr Thr Val Leu Phe Lys Phe Lys Glu
1               5                   10                  15

Thr Tyr Gly Val Ser Phe Met Glu Leu Val Arg Pro Phe Lys
            20                  25                  30

<210> SEQ ID NO 49
<211> LENGTH: 30
```

```
<212> TYPE: PRT
<213> ORGANISM: Human papillomavirus type 52

<400> SEQUENCE: 49

Leu Thr Val Ser Lys Leu Met Ser Gln Leu Leu Asn Ile Pro Glu Thr
1               5                   10                  15

His Met Val Ile Glu Pro Pro Lys Leu Arg Ser Ala Thr Cys
            20                  25                  30

<210> SEQ ID NO 50
<211> LENGTH: 30
<212> TYPE: PRT
<213> ORGANISM: Human papillomavirus type 58

<400> SEQUENCE: 50

Leu His Asn Ser Asn Thr Lys Ala Thr Leu Leu Tyr Lys Phe Lys Glu
1               5                   10                  15

Ala Tyr Gly Val Ser Phe Met Glu Leu Val Arg Pro Phe Lys
            20                  25                  30

<210> SEQ ID NO 51
<211> LENGTH: 30
<212> TYPE: PRT
<213> ORGANISM: Human papillomavirus type 58

<400> SEQUENCE: 51

Leu Thr Val Ala Lys Leu Met Ser Asn Leu Leu Ser Ile Pro Glu Thr
1               5                   10                  15

Cys Met Ile Ile Glu Pro Pro Lys Leu Arg Ser Gln Ala Cys
            20                  25                  30

<210> SEQ ID NO 52
<211> LENGTH: 30
<212> TYPE: PRT
<213> ORGANISM: Human papillomavirus type 59

<400> SEQUENCE: 52

Leu His Ser Lys Asn Lys Lys Ala Ala Met Tyr Ala Lys Phe Lys Glu
1               5                   10                  15

Leu Tyr Gly Leu Ser Phe Gln Asp Leu Val Arg Thr Phe Lys
            20                  25                  30

<210> SEQ ID NO 53
<211> LENGTH: 30
<212> TYPE: PRT
<213> ORGANISM: Human papillomavirus type 59

<400> SEQUENCE: 53

Ile Thr Val Ala Lys Gly Leu Ser Thr Leu Leu His Val Pro Asp Thr
1               5                   10                  15

Cys Met Leu Ile Glu Pro Pro Lys Leu Arg Ser Gly Val Ala
            20                  25                  30

<210> SEQ ID NO 54
<211> LENGTH: 30
<212> TYPE: PRT
<213> ORGANISM: Human papillomavirus type 66

<400> SEQUENCE: 54

Phe Lys Ser Ser Asn Val Gln Gly Arg Leu His Phe Lys Phe Lys Glu
1               5                   10                  15

Val Tyr Gly Val Pro Tyr Thr Glu Leu Val Arg Thr Phe Lys
```

<210> SEQ ID NO 55
<211> LENGTH: 30
<212> TYPE: PRT
<213> ORGANISM: Human papillomavirus type 66

<400> SEQUENCE: 55

Lys Thr Ile Thr Lys Ser Leu Ser Ser Ile Leu Asn Val Pro Gln Glu
1               5                   10                  15
Gln Met Leu Ile Gln Pro Pro Lys Leu Arg Ser Pro Ala Val
            20                  25                  30

<210> SEQ ID NO 56
<211> LENGTH: 30
<212> TYPE: PRT
<213> ORGANISM: Human papillomavirus type 73

<400> SEQUENCE: 56

Leu Gln Arg Asn Asn Ala Lys Ala Ala Leu Leu Ala Lys Phe Lys Glu
1               5                   10                  15
Val Tyr Gly Leu Ser Tyr Met Glu Leu Val Arg Pro Tyr Lys
            20                  25                  30

<210> SEQ ID NO 57
<211> LENGTH: 30
<212> TYPE: PRT
<213> ORGANISM: Human papillomavirus type 73

<400> SEQUENCE: 57

Leu Thr Val Gln Lys Leu Leu Ser Ser Leu Leu Asn Val Thr Gln Glu
1               5                   10                  15
Arg Met Leu Ile Glu Pro Pro Arg Leu Arg Ser Thr Pro Cys
            20                  25                  30

<210> SEQ ID NO 58
<211> LENGTH: 52
<212> TYPE: PRT
<213> ORGANISM: Human papillomavirus type 16

<400> SEQUENCE: 58

Gly Asn Pro Val Tyr Glu Leu Asn Asp Lys Asn Trp Lys Ser Phe Phe
1               5                   10                  15
Ser Arg Thr Trp Ser Arg Leu Ser Leu His Glu Asp Glu Asp Lys Glu
            20                  25                  30
Asn Asp Gly Asp Ser Leu Pro Thr Phe Lys Cys Val Ser Gly Gln Asn
        35                  40                  45
Thr Asn Thr Leu
    50

<210> SEQ ID NO 59
<211> LENGTH: 53
<212> TYPE: PRT
<213> ORGANISM: Human papillomavirus type 18

<400> SEQUENCE: 59

Gly Asn Pro Val Tyr Glu Ile Asn Asp Lys Asn Trp Lys Cys Phe Phe
1               5                   10                  15
Glu Arg Thr Trp Ser Arg Leu Asp Leu His Glu Glu Glu Glu Asp Ala
            20                  25                  30
Asp Thr Glu Gly Asn Pro Phe Gly Thr Phe Lys Leu Arg Ala Gly Gln

Asn His Arg Pro Leu
    50

<210> SEQ ID NO 60
<211> LENGTH: 51
<212> TYPE: PRT
<213> ORGANISM: Human papillomavirus type 26

<400> SEQUENCE: 60

Gly Asn Pro Val Tyr Ala Leu Thr Asp Val Asn Trp Lys Ser Phe Phe
1               5                   10                  15

Ser Thr Thr Trp Ser Arg Leu Asp Leu Glu Glu Asp Ala Asp Lys Glu
            20                  25                  30

Asn Gly Glu Pro Leu Pro Ala Phe Lys Cys Val Pro Gly Glu Asn Thr
        35                  40                  45

Arg Leu Leu
    50

<210> SEQ ID NO 61
<211> LENGTH: 52
<212> TYPE: PRT
<213> ORGANISM: Human papillomavirus type 31

<400> SEQUENCE: 61

Gly Asn Pro Val Tyr Glu Leu Ser Asp Lys Asn Trp Lys Ser Phe Phe
1               5                   10                  15

Ser Arg Thr Trp Cys Arg Leu Asn Leu His Glu Glu Glu Asp Lys Glu
            20                  25                  30

Asn Asp Gly Asp Ser Phe Ser Thr Phe Lys Cys Val Ser Gly Gln Asn
        35                  40                  45

Ile Arg Thr Leu
    50

<210> SEQ ID NO 62
<211> LENGTH: 54
<212> TYPE: PRT
<213> ORGANISM: Human papillomavirus type 33

<400> SEQUENCE: 62

Gly Asn Pro Val Tyr Ala Ile Asn Asp Glu Asn Trp Lys Ser Phe Phe
1               5                   10                  15

Ser Arg Thr Trp Cys Lys Leu Asp Leu Ile Glu Glu Asp Lys Glu
            20                  25                  30

Asn His Gly Gly Asn Ile Ser Thr Phe Lys Cys Ser Ala Gly Glu Asn
        35                  40                  45

Thr Arg Ser Leu Arg Ser
    50

<210> SEQ ID NO 63
<211> LENGTH: 54
<212> TYPE: PRT
<213> ORGANISM: Human papillomavirus type 35

<400> SEQUENCE: 63

Gly Asn Pro Val Tyr Gly Leu Asn Asp Lys Asn Trp Lys Ser Phe Phe
1               5                   10                  15

Ser Arg Thr Trp Cys Arg Leu Asn Leu His Glu Glu Glu Asp Lys Glu
            20                  25                  30

```
Asn Asp Gly Asp Ala Phe Pro Ala Phe Lys Cys Val Ser Gly Gln Asn
        35                  40                  45

Thr Arg Thr Leu Arg Asp
 50

<210> SEQ ID NO 64
<211> LENGTH: 53
<212> TYPE: PRT
<213> ORGANISM: Human papillomavirus type 39

<400> SEQUENCE: 64

Arg Asn Pro Val Tyr Thr Ile Asn Asp Lys Asn Trp Lys Cys Phe Phe
 1               5                  10                  15

Glu Lys Thr Trp Cys Arg Leu Asp Leu Gln Gln Asp Glu Asp Glu Gly
            20                  25                  30

Asp Asn Asp Glu Asn Thr Phe Thr Thr Phe Lys Cys Val Thr Gly Gln
        35                  40                  45

Asn Thr Arg Ile Leu
 50

<210> SEQ ID NO 65
<211> LENGTH: 53
<212> TYPE: PRT
<213> ORGANISM: Human papillomavirus type 45

<400> SEQUENCE: 65

Gly Asn Pro Val Tyr Glu Ile Asn Asp Lys Asn Trp Lys Cys Phe Phe
 1               5                  10                  15

Glu Arg Thr Trp Ser Arg Leu Asp Leu His Glu Asp Asp Glu Asp Ala
            20                  25                  30

Asp Thr Glu Gly Ile Pro Phe Gly Thr Phe Lys Cys Val Thr Gly Gln
        35                  40                  45

Asn Thr Arg Pro Leu
 50

<210> SEQ ID NO 66
<211> LENGTH: 51
<212> TYPE: PRT
<213> ORGANISM: Human papillomavirus type 51

<400> SEQUENCE: 66

Gly Asn Ala Val Tyr Thr Leu Asn Asp Glu Asn Trp Lys Asn Phe Phe
 1               5                  10                  15

Ser Thr Thr Trp Ser Arg Leu Asp Leu Glu Glu Glu Glu Asp Lys Glu
            20                  25                  30

Asn Gly Asp Pro Met Pro Pro Phe Lys Cys Val Pro Gly Glu Asn Thr
        35                  40                  45

Arg Leu Leu
 50

<210> SEQ ID NO 67
<211> LENGTH: 54
<212> TYPE: PRT
<213> ORGANISM: Human papillomavirus type 52

<400> SEQUENCE: 67

Gly Asn Pro Ile Tyr Glu Ile Asn Asn Glu Asn Trp Lys Ser Phe Phe
 1               5                  10                  15

Ser Arg Thr Trp Cys Lys Leu Asp Leu Ile Gln Glu Glu Asp Lys Glu
            20                  25                  30
```

Asn Asp Gly Val Asp Thr Gly Thr Phe Lys Cys Ser Ala Gly Lys Asn
            35                  40                  45

Thr Arg Ser Ile Arg Ser
        50

<210> SEQ ID NO 68
<211> LENGTH: 54
<212> TYPE: PRT
<213> ORGANISM: Human papillomavirus type 58

<400> SEQUENCE: 68

Gly Asn Pro Val Tyr Lys Ile Asn Asp Glu Asn Trp Lys Ser Phe Phe
1               5                   10                  15

Ser Arg Thr Trp Cys Lys Leu Gly Leu Ile Glu Glu Glu Asp Lys Glu
            20                  25                  30

Asn Asp Gly Gly Asn Ile Ser Thr Phe Lys Cys Ser Ala Gly Gln Asn
            35                  40                  45

Pro Arg His Ile Arg Ser
        50

<210> SEQ ID NO 69
<211> LENGTH: 53
<212> TYPE: PRT
<213> ORGANISM: Human papillomavirus type 59

<400> SEQUENCE: 69

Arg Asn Pro Val Tyr Thr Ile Asn Asp Arg Asn Trp Lys Cys Phe Phe
1               5                   10                  15

Glu Arg Thr Trp Cys Arg Leu Asp Leu Asn Glu Glu Glu Glu Asp Ala
            20                  25                  30

Asp Ser Asp Gly His Pro Phe Ala Ala Phe Lys Cys Val Thr Gly Ser
            35                  40                  45

Asn Ile Arg Thr Leu
        50

<210> SEQ ID NO 70
<211> LENGTH: 52
<212> TYPE: PRT
<213> ORGANISM: Human papillomavirus type 66

<400> SEQUENCE: 70

Gly Asn Pro Val Tyr Glu Leu Ser Asn Val Asn Trp Lys Cys Phe Phe
1               5                   10                  15

Glu Arg Thr Trp Ser Arg Leu Asn Leu Asp Asn Asp Glu Asp Lys Glu
            20                  25                  30

Asn Asn Gly Asp Ser Ile Pro Thr Phe Arg Cys Val Pro Glu Gln Asn
            35                  40                  45

Thr Arg Leu Leu
        50

<210> SEQ ID NO 71
<211> LENGTH: 52
<212> TYPE: PRT
<213> ORGANISM: Human papillomavirus type 73

<400> SEQUENCE: 71

Gly Asn Pro Leu Tyr Gln Leu Thr Asn Glu Asn Trp Lys Ala Phe Phe
1               5                   10                  15

Thr Lys Thr Trp Ser Lys Leu Asp Leu Thr Glu Asp Asp Asp Lys Glu

```
                20                  25                  30
Asn Asp Gly Asp Thr Val Gln Thr Phe Lys Cys Val Ser Gly Arg Asn
        35                  40                  45

Pro Arg Thr Val
    50

<210> SEQ ID NO 72
<211> LENGTH: 91
<212> TYPE: PRT
<213> ORGANISM: Human papillomavirus type 54/52

<400> SEQUENCE: 72

Leu His Leu Tyr Leu Val Pro Lys Arg His Cys Gln Tyr Pro Leu Leu
1               5                   10                  15

Ala Leu Leu Asn Thr Pro Asp Gln Pro Ile Pro His His Val Pro Thr
            20                  25                  30

Thr Pro Gln Lys Gln Ser Arg Ala Arg Arg Leu Glu Asn Glu Leu
        35                  40                  45

Glu Ser Thr Ala Gln Thr Ser Asn His Thr Ala Pro Gln Thr Pro Trp
    50                  55                  60

Ala Val Thr Thr Thr Gly Thr Ser Val Thr Ile Thr Thr Arg Thr Lys
65                  70                  75                  80

Asp Gly Thr Gln Val Val Val Thr Leu His Leu
                85                  90

<210> SEQ ID NO 73
<211> LENGTH: 85
<212> TYPE: PRT
<213> ORGANISM: Human papillomavirus type 58/33

<400> SEQUENCE: 73

Leu His Leu Tyr Leu Val Ile Lys Tyr Pro Leu Leu Lys Leu Leu Thr
1               5                   10                  15

Gln Arg Pro Pro Arg Pro Pro Thr Thr Lys Val His Arg Gly Gln Ser
            20                  25                  30

Asp Asp Asp Ser Ile Tyr Gln Thr Pro Glu Thr Thr Pro Ser Thr Pro
        35                  40                  45

Gln Ser Ile Gln Thr Ala Pro Trp Thr Val Asp His Glu Glu Glu Asp
    50                  55                  60

Tyr Thr Val Gln Leu Thr Val His Thr Lys Gly Gly Thr Cys Val Val
65                  70                  75                  80

Leu Lys Phe His Leu
                85

<210> SEQ ID NO 74
<211> LENGTH: 92
<212> TYPE: PRT
<213> ORGANISM: Human papillomavirus type 16

<400> SEQUENCE: 74

Leu His Leu Cys Leu Ala Ala Thr Lys Tyr Pro Leu Leu Lys Leu Leu
1               5                   10                  15

Gly Ser Thr Trp Pro Thr Thr Pro Arg Pro Ile Pro Lys Pro Ser
            20                  25                  30

Pro Trp Ala Pro Lys Lys His Arg Arg Leu Ser Ser Asp Gln Asp Gln
        35                  40                  45

Ser Gln Thr Pro Glu Thr Pro Ala Thr Pro Leu Ser Cys Cys Thr Glu
    50                  55                  60
```

```
Thr Gln Trp Thr Val Leu Gln Ser Ser Leu His Leu Thr Ala His Thr
 65                  70                  75                  80

Lys Asp Gly Leu Thr Val Ile Val Thr Leu His Pro
                 85                  90

<210> SEQ ID NO 75
<211> LENGTH: 99
<212> TYPE: PRT
<213> ORGANISM: Human papillomavirus type 31

<400> SEQUENCE: 75

Leu Asn Leu Tyr Leu Ala Val Thr Lys Tyr Pro Leu Gly Leu Leu
 1               5                  10                  15

Gln Ser Tyr Gln Gln Pro Thr Thr Pro Pro His Arg Ile Pro Lys Pro
                 20                  25                  30

Ala Pro Trp Ala Pro Val Lys Val Cys Gly Gly Arg Arg Leu Leu
             35                  40                  45

Ser Asp Gln Glu Gln Ser Gln Ser Thr Glu Thr Pro Thr Thr Pro Thr
     50                  55                  60

Ser Cys Cys Glu Ala Thr Pro Trp Thr Val Ser Thr Val Gly Leu Ser
 65                  70                  75                  80

Val Gln Leu His Ala Gln Thr Lys Gln Gly Leu Ser Val Val Leu Gln
                 85                  90                  95

Leu His Leu

<210> SEQ ID NO 76
<211> LENGTH: 93
<212> TYPE: PRT
<213> ORGANISM: Human papillomavirus type 35

<400> SEQUENCE: 76

Leu Asn Leu Tyr Leu Ala Ala Gln Asn Tyr Pro Leu Leu Lys Leu Leu
 1               5                  10                  15

His Ser Tyr Thr Pro Thr Thr Pro Arg Pro Ile Pro Lys Pro Ala
                 20                  25                  30

Pro Trp Ala Pro Gln Lys Pro Arg Arg Gln Ile Thr Asn Asp Phe Glu
             35                  40                  45

Gly Val Pro Ser Ser Pro Thr Thr Pro Ser Glu Cys Asp Ser Val
     50                  55                  60

Pro Trp Thr Val Leu Thr Glu Gly Ser Thr Leu His Leu Thr Ala Gln
 65                  70                  75                  80

Thr Lys Thr Gly Val Val Val Val Gln Leu His Leu
                 85                  90

<210> SEQ ID NO 77
<211> LENGTH: 87
<212> TYPE: PRT
<213> ORGANISM: Human papillomavirus type 51

<400> SEQUENCE: 77

Met Tyr Leu Val Pro Ala Ala Thr Arg Tyr Pro Leu Leu Gln Leu Leu
 1               5                  10                  15

Asn Asn Tyr Gln Thr Pro Gln Arg Pro Ile Pro Leu Pro Ala Trp
                 20                  25                  30

Ala Pro Lys Lys Pro Arg His Asn Ser Glu Asn Asp Ser Asp Leu Leu
             35                  40                  45

Ser Pro Thr Pro Pro Gln Ser Pro His Cys Pro Trp Thr Ile Gln Thr
```

```
            50                  55                  60
Thr Lys Tyr Thr Val Glu Val Glu Ala Leu Thr Leu Glu Gly Thr Lys
 65                  70                  75                  80

Val Gln Leu Arg Leu Arg Leu
                85

<210> SEQ ID NO 78
<211> LENGTH: 86
<212> TYPE: PRT
<213> ORGANISM: Human papillomavirus type 18

<400> SEQUENCE: 78

Leu Cys Ala Val Pro Val Thr Thr Arg Tyr Pro Leu Leu Ser Leu Leu
 1               5                   10                  15

Asn Ser Tyr Ser Thr Pro Pro His Arg Ile Pro Ala Pro Cys Pro Trp
                20                  25                  30

Ala Pro Gln Arg Pro Thr Ala Arg Arg Leu Leu His Asp Leu Asp
            35                  40                  45

Thr Val Asp Ser Arg Arg Ser Ser Ile Val Asp Leu Ser Thr His Phe
 50                  55                  60

Ser Val Gln Leu His Leu Gln Ala Thr Thr Lys Asp Gly Asn Ser Val
 65                  70                  75                  80

Val Val Thr Leu Arg Leu
                85

<210> SEQ ID NO 79
<211> LENGTH: 89
<212> TYPE: PRT
<213> ORGANISM: Human papillomavirus type 39

<400> SEQUENCE: 79

Leu Cys Ala Val Pro Val Thr Asp Arg Tyr Pro Leu Leu Asn Leu Leu
 1               5                   10                  15

Pro Asn Tyr Gln Thr Pro Pro Arg Pro Ile Pro Pro Gln Gln Pro His
                20                  25                  30

Ala Pro Lys Lys Gln Ser Arg Arg Leu Glu Ser Asp Leu Asp Ser
            35                  40                  45

Val Gln Ser Gln Ser Pro Leu Ser Pro Thr Glu Cys Pro Trp Thr Ile
 50                  55                  60

Leu Thr Thr His Ser Thr Val Thr Val Gln Ala Thr Thr Gln Asp Gly
 65                  70                  75                  80

Thr Ser Val Val Val Thr Leu Arg Leu
                85

<210> SEQ ID NO 80
<211> LENGTH: 94
<212> TYPE: PRT
<213> ORGANISM: Human papillomavirus type 67/68/66

<400> SEQUENCE: 80

Leu His Leu Cys Leu Val Thr Lys Tyr Pro Leu Leu Arg Leu Leu Pro
 1               5                   10                  15

Gly Tyr His Thr Pro Gln Lys Arg Ile Pro Leu Pro Pro Arg Ala
                20                  25                  30

Pro Lys Lys Asn Arg Arg Leu Pro Asn Asp Asp Leu Thr Ser Gln
            35                  40                  45

Thr Ser Ala Thr Thr Pro Ser Thr Pro Gln Ser Tyr Cys Ala Asp Asn
 50                  55                  60
```

Gly Pro Trp Thr Val His Arg Trp Gly Ser Ser Leu Asp Leu Ser Ala
65                  70                  75                  80

Gln Thr Lys Asp Gly Val Cys Val His Leu Thr Leu His Leu
                85                  90

<210> SEQ ID NO 81
<211> LENGTH: 84
<212> TYPE: PRT
<213> ORGANISM: Human papillomavirus type 51

<400> SEQUENCE: 81

Leu Tyr Arg His Ile Val Thr Ile Ala Val Phe Ile Ile Leu Leu Phe
1               5                   10                  15

Val Leu Cys Leu Cys Val Cys Leu Val Leu Cys Cys Leu Leu Pro Leu
                20                  25                  30

Leu Leu Ser Gln Tyr Val Phe Ala Ala Ala Leu Leu Leu Ile Leu Cys
            35                  40                  45

Phe Trp Phe Val Val Ala Thr Ser Gln Leu Thr Thr Phe Phe Val Tyr
50                  55                  60

Leu Ile Phe Phe Tyr Leu Pro Cys Leu Leu His Leu Tyr Thr Phe
65                  70                  75                  80

Leu Leu Leu Gln

<210> SEQ ID NO 82
<211> LENGTH: 97
<212> TYPE: PRT
<213> ORGANISM: Human papillomavirus type 69

<400> SEQUENCE: 82

Cys Asn Ile Tyr Thr Ser His Lys Pro Ile Cys Ala Ala Asn Cys Ile
1               5                   10                  15

Tyr Ile Thr Ile Leu Leu Leu Val Ile Val Phe Val Leu Cys Val Cys
                20                  25                  30

Val Cys Leu Leu Leu Cys Arg Leu Leu Pro Leu Leu Leu Ser Ile His
            35                  40                  45

Val Phe Ala Ala His Leu Leu Ile Ile Ile Cys Phe Trp Phe Val Val
50                  55                  60

Ser Thr Ser Phe Thr Ala Thr Phe Phe Val Tyr Ile Cys Leu Phe Tyr
65                  70                  75                  80

Ile Pro Ala Phe Leu Leu His Phe Tyr Ala Val Ile Leu Leu Pro Asn
                85                  90                  95

Gly

<210> SEQ ID NO 83
<211> LENGTH: 75
<212> TYPE: PRT
<213> ORGANISM: Human papillomavirus type 52

<400> SEQUENCE: 83

Met Leu Gly Leu Phe Val Phe Cys Phe Ile Leu Leu Met Val Phe Cys
1               5                   10                  15

Ala Val Leu Arg Pro Leu Leu Leu Ser Ile Ser Val Tyr Ala Gln Val
                20                  25                  30

Leu Val Leu Val Leu Leu Leu Trp Val Ser Ile Gly Ser Pro Phe Lys
            35                  40                  45

Val Phe Phe Leu Tyr Leu Leu Phe Leu Tyr Phe Pro Met Phe Cys Ile
50                  55                  60

His Cys His Ala Gln Tyr Leu Ala Gln Leu Gln
65                  70                  75

<210> SEQ ID NO 84
<211> LENGTH: 73
<212> TYPE: PRT
<213> ORGANISM: Human papillomavirus type 67

<400> SEQUENCE: 84

Met Leu Ala Ile Phe Val Phe Ala Phe Val Leu Leu Cys Phe Cys
1               5                   10                  15

Ile Val Leu Arg Pro Leu Leu Ser Ile Tyr Val Tyr Ala Leu Leu
                20                  25                  30

Leu Val Leu Val Leu Val Leu Trp Gly Phe Ile Gly Ser Pro Leu Arg
            35                  40                  45

Val Phe Leu Ala Tyr Leu Ile Phe Leu Tyr Leu Pro Met Met Cys Ile
        50                  55                  60

His Leu His Ala Gln Tyr Ile Val Ser
65                  70

<210> SEQ ID NO 85
<211> LENGTH: 76
<212> TYPE: PRT
<213> ORGANISM: Human papillomavirus type 58

<400> SEQUENCE: 85

Met Ile Leu Pro Ile Phe Val Val Cys Phe Ile Leu Phe Leu Cys Leu
1               5                   10                  15

Cys Ile Phe Leu Arg Pro Leu Val Leu Ser Ile Ser Ile Tyr Ala Trp
                20                  25                  30

Leu Leu Val Leu Val Leu Leu Leu Trp Val Ser Val Gly Ser Ala Leu
            35                  40                  45

Arg Ile Phe Phe Cys Tyr Leu Ile Phe Leu Tyr Ile Pro Met Met Cys
        50                  55                  60

Ile Asn Phe His Ala Gln Tyr Leu Thr Gln Gln Asp
65                  70                  75

<210> SEQ ID NO 86
<211> LENGTH: 75
<212> TYPE: PRT
<213> ORGANISM: Human papillomavirus type 33

<400> SEQUENCE: 86

Met Ile Phe Val Phe Val Leu Cys Phe Ile Leu Phe Leu Cys Leu Ser
1               5                   10                  15

Leu Leu Leu Arg Pro Leu Ile Leu Ser Ile Ser Thr Tyr Ala Trp Leu
                20                  25                  30

Leu Val Leu Val Leu Leu Leu Trp Val Phe Val Gly Ser Pro Leu Lys
            35                  40                  45

Ile Phe Phe Cys Tyr Leu Leu Phe Leu Tyr Leu Pro Met Met Cys Ile
        50                  55                  60

Asn Phe His Ala Gln His Met Thr Gln Gln Glu
65                  70                  75

<210> SEQ ID NO 87
<211> LENGTH: 83
<212> TYPE: PRT
<213> ORGANISM: Human papillomavirus type 16

```
<400> SEQUENCE: 87

Met Thr Asn Leu Asp Thr Ala Ser Thr Thr Leu Leu Ala Cys Phe Leu
1               5                   10                  15

Leu Cys Phe Cys Val Leu Leu Cys Val Cys Leu Leu Ile Arg Pro Leu
            20                  25                  30

Leu Leu Ser Val Ser Thr Tyr Thr Ser Leu Ile Ile Leu Val Leu Leu
        35                  40                  45

Leu Trp Ile Thr Ala Ala Ser Ala Phe Arg Cys Phe Ile Val Tyr Ile
    50                  55                  60

Ile Phe Val Tyr Ile Pro Leu Phe Leu Ile His Thr His Ala Arg Phe
65                  70                  75                  80

Leu Ile Thr

<210> SEQ ID NO 88
<211> LENGTH: 83
<212> TYPE: PRT
<213> ORGANISM: Human papillomavirus type 35

<400> SEQUENCE: 88

Met Ile Asp Leu Thr Ala Ser Ser Thr Val Leu Leu Cys Phe Leu Leu
1               5                   10                  15

Cys Phe Cys Val Leu Leu Cys Leu Cys Leu Leu Val Arg Ser Leu Leu
            20                  25                  30

Leu Ser Val Ser Leu Tyr Ser Ala Leu Ile Leu Leu Val Leu Ile Leu
        35                  40                  45

Trp Val Thr Val Ala Thr Pro Leu Arg Cys Phe Cys Cys Phe Leu Cys
    50                  55                  60

Phe Leu Tyr Ile Pro Met Gly Met Ile Asn Ala His Ala Gln Tyr Leu
65                  70                  75                  80

Ala Val Gln

<210> SEQ ID NO 89
<211> LENGTH: 84
<212> TYPE: PRT
<213> ORGANISM: Human papillomavirus type 31

<400> SEQUENCE: 89

Met Ile Glu Leu Asn Ile Ser Thr Val Ser Ile Val Leu Cys Phe Leu
1               5                   10                  15

Leu Cys Phe Cys Val Leu Leu Phe Val Cys Leu Val Ile Arg Pro Leu
            20                  25                  30

Val Leu Ser Val Ser Val Tyr Ala Thr Leu Leu Leu Leu Ile Val Ile
        35                  40                  45

Leu Trp Val Ile Ala Thr Ser Pro Leu Arg Cys Phe Cys Ile Tyr Val
    50                  55                  60

Val Phe Ile Tyr Ile Pro Leu Phe Val Ile His Thr His Ala Ser Phe
65                  70                  75                  80

Leu Ser Gln Gln

<210> SEQ ID NO 90
<211> LENGTH: 74
<212> TYPE: PRT
<213> ORGANISM: Human papillomavirus type 73

<400> SEQUENCE: 90

Met Ile Leu Cys Ile Phe Val Phe Leu Phe Cys Val Gly Phe Cys Leu
1               5                   10                  15
```

```
Cys Leu Cys Val Ser Leu Ala Val Ser Val Tyr Ile Tyr Pro Trp Leu
            20                  25                  30

Leu Val Leu Ile Ile Ile Thr Phe Ile His Val Ser Gln Ser Leu Leu
            35                  40                  45

Lys Val Phe Phe Leu Tyr Val Leu Val Phe Tyr Ile Pro Met Ala Leu
            50                  55                  60

Val His Tyr His Ala Thr Leu Gln Ile Thr
 65                  70
```

<210> SEQ ID NO 91
<211> LENGTH: 85
<212> TYPE: PRT
<213> ORGANISM: Human papillomavirus type 66

<400> SEQUENCE: 91

```
Ser Pro Tyr Ile Ala Thr Ile Asp Phe Cys Val Ile Cys Val Phe Ala
 1               5                  10                  15

Leu Cys Phe Cys Val Cys Leu Cys Val Cys His Phe Val Pro Leu Leu
            20                  25                  30

Leu Ser Ala Ser Leu Phe Thr Ser Cys Leu Ile Leu Ile Ile Leu Phe
            35                  40                  45

Trp Phe Val Val Ala Thr Ser Phe Phe Asp Thr Phe Ile Leu Phe Leu
            50                  55                  60

Leu Phe Phe Tyr Ile Pro Thr Leu Cys Ile Tyr Cys His Ala Leu Trp
 65                  70                  75                  80

Leu Ile Asn His Leu
                 85
```

<210> SEQ ID NO 92
<211> LENGTH: 73
<212> TYPE: PRT
<213> ORGANISM: Human papillomavirus type 45

<400> SEQUENCE: 92

```
Met Leu Ser Leu Val Phe Leu Leu Cys Phe Ser Val Cys Leu Tyr Val
 1               5                  10                  15

Cys Cys Asn Val Pro Leu Val Gln Ser Val Tyr Val Cys Ala Phe Ala
            20                  25                  30

Trp Leu Leu Val Phe Leu Phe Ile Val Val Ile Thr Ser Pro Leu Thr
            35                  40                  45

Ala Phe Ala Val Tyr Ile Cys Cys Tyr Leu Leu Pro Met Phe Val Leu
            50                  55                  60

His Met His Ala Leu His Thr Ile Gln
 65                  70
```

<210> SEQ ID NO 93
<211> LENGTH: 73
<212> TYPE: PRT
<213> ORGANISM: Human papillomavirus type 18

<400> SEQUENCE: 93

```
Met Leu Ser Leu Ile Phe Leu Phe Cys Phe Cys Val Cys Met Tyr Val
 1               5                  10                  15

Cys Cys His Val Pro Leu Leu Pro Ser Val Cys Met Cys Ala Tyr Ala
            20                  25                  30

Trp Val Leu Val Phe Val Tyr Ile Val Val Ile Thr Ser Pro Ala Thr
            35                  40                  45
```

Ala Phe Thr Val Tyr Val Phe Cys Phe Leu Leu Pro Met Leu Leu Leu
    50                  55                  60

His Ile His Ala Ile Leu Ser Leu Gln
 65                  70

<210> SEQ ID NO 94
<211> LENGTH: 48
<212> TYPE: PRT
<213> ORGANISM: Human papillomavirus type 68M

<400> SEQUENCE: 94

Met His Val Cys Val Tyr Val Trp Ile Leu Val Phe Val Phe Ile Leu
  1               5                  10                  15

Val Arg Thr Thr Pro Leu Glu Val Phe Ala Val Tyr Ile Leu Phe Phe
                 20                  25                  30

Leu Leu Pro Met Trp Val Leu His Ser Phe Ala Arg Tyr Ser Met Pro
             35                  40                  45

<210> SEQ ID NO 95
<211> LENGTH: 72
<212> TYPE: PRT
<213> ORGANISM: Human papillomavirus type 39

<400> SEQUENCE: 95

Met Ile Leu Leu Val Phe Leu Val Trp Phe Gly Val Cys Ile Tyr Ile
  1               5                  10                  15

Cys Cys Asn Val Pro Leu Leu Pro Ser Val His Val Cys Ala Tyr Val
                 20                  25                  30

Trp Ile Ile Val Phe Val Phe Ile Leu Ile Arg Thr Thr Pro Leu Glu
             35                  40                  45

Val Phe Phe Val Tyr Leu Leu Phe Phe Val Leu Pro Met Trp Leu Leu
    50                  55                  60

His Arg Leu Ala Met Asp Met Ile
 65                  70

<210> SEQ ID NO 96
<211> LENGTH: 73
<212> TYPE: PRT
<213> ORGANISM: Human papillomavirus type 59

<400> SEQUENCE: 96

Met Ile Thr Leu Val Phe Val Cys Cys Val Cys Val Cys Leu Cys Val
  1               5                  10                  15

Cys Cys Asn Val Pro Leu Leu Gln Ser Val Tyr Met Cys Ala Tyr Thr
                 20                  25                  30

Trp Leu Leu Val Phe Val Tyr Ile Val Val Ile Thr Ser Ser Tyr Glu
             35                  40                  45

Cys Phe Leu Leu Tyr Ile Leu Phe Phe Ile Ile Pro Leu Leu Leu Leu
    50                  55                  60

Tyr Ala His Ala Ile Leu Ser Ile Gln
 65                  70

<210> SEQ ID NO 97
<211> LENGTH: 158
<212> TYPE: PRT
<213> ORGANISM: Human papillomavirus type 16

<400> SEQUENCE: 97

Met His Gln Lys Arg Thr Ala Met Phe Gln Asp Pro Gln Glu Arg Pro
  1               5                  10                  15

```
Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 98
<211> LENGTH: 160
<212> TYPE: PRT
<213> ORGANISM: Human papillomavirus type 59

<400> SEQUENCE: 98

Met Ala Arg Phe Glu Asp Pro Thr Gln Arg Pro Tyr Lys Leu Pro Asp
1               5                   10                  15

Leu Ser Thr Thr Leu Asn Ile Pro Leu His Asp Ile Arg Ile Asn Cys
            20                  25                  30

Val Phe Cys Lys Gly Glu Leu Gln Glu Arg Glu Val Phe Glu Phe Ala
        35                  40                  45

Phe Asn Asp Leu Phe Ile Val Tyr Arg Asp Cys Thr Pro Tyr Ala Ala
    50                  55                  60

Cys Leu Lys Cys Ile Ser Phe Tyr Ala Arg Val Arg Glu Leu Arg Tyr
65                  70                  75                  80

Tyr Arg Asp Ser Val Tyr Gly Glu Thr Leu Glu Ala Glu Thr Lys Thr
                85                  90                  95

Pro Leu His Glu Leu Leu Ile Arg Cys Tyr Arg Cys Leu Lys Pro Leu
            100                 105                 110

Cys Pro Thr Asp Lys Leu Lys His Ile Thr Glu Lys Arg Arg Phe His
        115                 120                 125

Asn Ile Ala Gly Ile Tyr Thr Gly Gln Cys Arg Gly Cys Arg Thr Arg
    130                 135                 140

Ala Arg His Leu Arg Gln Gln Arg Gln Ala Arg Ser Glu Thr Leu Val
145                 150                 155                 160

<210> SEQ ID NO 99
<211> LENGTH: 158
<212> TYPE: PRT
<213> ORGANISM: Human papillomavirus type 39

<400> SEQUENCE: 99

Met Ala Arg Phe His Asn Pro Ala Glu Arg Pro Tyr Lys Leu Pro Asp
1               5                   10                  15

Leu Cys Thr Thr Leu Asp Thr Thr Leu Gln Asp Ile Thr Ile Ala Cys
            20                  25                  30
```

```
Val Tyr Cys Arg Arg Pro Leu Gln Gln Thr Glu Val Tyr Glu Phe Ala
            35                  40                  45

Phe Ser Asp Leu Tyr Val Val Tyr Arg Asp Gly Glu Pro Leu Ala Ala
 50                  55                  60

Cys Gln Ser Cys Ile Lys Phe Tyr Ala Lys Ile Arg Glu Leu Arg Tyr
65                  70                  75                  80

Tyr Ser Asp Ser Val Tyr Ala Thr Thr Leu Glu Asn Ile Thr Asn Thr
                85                  90                  95

Lys Leu Tyr Asn Leu Leu Ile Arg Cys Met Cys Cys Leu Lys Pro Leu
                100                 105                 110

Cys Pro Ala Glu Lys Leu Arg His Leu Asn Ser Lys Arg Arg Phe His
                115                 120                 125

Lys Ile Ala Gly Ser Tyr Thr Gly Gln Cys Arg Arg Cys Trp Thr Thr
                130                 135                 140

Lys Arg Glu Asp Arg Arg Leu Thr Arg Arg Glu Thr Gln Val
145                 150                 155

<210> SEQ ID NO 100
<211> LENGTH: 158
<212> TYPE: PRT
<213> ORGANISM: Human papillomavirus type 45

<400> SEQUENCE: 100

Met Ala Arg Phe Asp Asp Pro Lys Gln Arg Pro Tyr Lys Leu Pro Asp
1               5                   10                  15

Leu Cys Thr Glu Leu Asn Thr Ser Leu Gln Asp Val Ser Ile Ala Cys
                20                  25                  30

Val Tyr Cys Lys Ala Thr Leu Glu Arg Thr Glu Val Tyr Gln Phe Ala
            35                  40                  45

Phe Lys Asp Leu Cys Ile Val Tyr Arg Asp Cys Ile Ala Tyr Ala Ala
 50                  55                  60

Cys His Lys Cys Ile Asp Phe Tyr Ser Arg Ile Arg Glu Leu Arg Tyr
65                  70                  75                  80

Tyr Ser Asn Ser Val Tyr Gly Glu Thr Leu Glu Lys Ile Thr Asn Thr
                85                  90                  95

Glu Leu Tyr Asn Leu Leu Ile Arg Cys Leu Arg Cys Gln Lys Pro Leu
                100                 105                 110

Asn Pro Ala Glu Lys Arg Arg His Leu Lys Asp Lys Arg Arg Phe His
                115                 120                 125

Ser Ile Ala Gly Gln Tyr Arg Gly Gln Cys Asn Thr Cys Cys Asp Gln
                130                 135                 140

Ala Arg Gln Glu Arg Leu Arg Arg Arg Glu Thr Gln Val
145                 150                 155

<210> SEQ ID NO 101
<211> LENGTH: 154
<212> TYPE: PRT
<213> ORGANISM: Human papillomavirus type 66

<400> SEQUENCE: 101

Met Asp Ser Ile Phe Ser Asn Thr Gln Glu Arg Pro Arg Ser Leu His
1               5                   10                  15

His Leu Ser Glu Val Leu Gln Ile Pro Leu Leu Asp Leu Arg Leu Ser
                20                  25                  30

Cys Val Tyr Cys Lys Lys Glu Leu Thr Ser Leu Glu Leu Tyr Arg Phe
            35                  40                  45
```

```
Ala Cys Ile Glu Leu Lys Leu Val Tyr Arg Asn Asn Trp Pro Tyr Ala
     50                  55                  60

Val Cys Arg Val Cys Leu Leu Phe Tyr Ser Lys Val Arg Lys Tyr Arg
 65                  70                  75                  80

Tyr Tyr Lys Tyr Ser Val Tyr Gly Ala Thr Leu Glu Ser Ile Thr Lys
                 85                  90                  95

Lys Gln Leu Ser Asp Leu Ser Ile Arg Cys Tyr Arg Cys Gln Cys Pro
            100                 105                 110

Leu Thr Pro Glu Glu Lys Gln Leu His Cys Glu His Lys Arg Arg Phe
            115                 120                 125

His Tyr Ile Ala Tyr Ala Trp Thr Gly Ser Cys Leu Gln Cys Trp Arg
        130                 135                 140

His Thr Ser Arg Gln Ala Thr Glu Ser Val
145                 150
```

<210> SEQ ID NO 102
<211> LENGTH: 150
<212> TYPE: PRT
<213> ORGANISM: Human papillomavirus type 26

<400> SEQUENCE: 102

```
Met Phe Glu Asp Pro Arg Glu Arg Pro Arg Thr Leu His Glu Leu Cys
 1               5                  10                  15

Glu Ser Leu Asn Thr Thr Leu Gln Asn Leu Gln Val Gln Cys Val Tyr
             20                  25                  30

Cys Lys Glu Thr Leu Gln Trp Ala Asp Val Tyr Asn Phe Ala Ile Cys
         35                  40                  45

Asp Leu Arg Val Val Tyr Arg Asp Arg Ser Pro Tyr Ala Ala Cys Lys
     50                  55                  60

Arg Cys Val Ile Phe Tyr Ser Lys Ile Thr Glu Tyr Arg Arg Tyr Thr
 65                  70                  75                  80

Cys Ser Val Tyr Gly Ala Thr Leu Glu Ala Leu Thr Lys Lys Ser Leu
                 85                  90                  95

Cys Asn Leu Leu Ile Arg Cys His Arg Cys Gln Met Pro Leu Gly Pro
            100                 105                 110

Glu Glu Lys Gln Arg Ile Val Asp Glu Lys Arg Arg Phe His Glu Ile
            115                 120                 125

Ala Gly Gln Trp Lys Gly Leu Cys Thr Asn Cys Trp Arg Pro Arg Arg
        130                 135                 140

Gln Thr Glu Thr Gln Val
145                 150
```

<210> SEQ ID NO 103
<211> LENGTH: 151
<212> TYPE: PRT
<213> ORGANISM: Human papillomavirus type 51

<400> SEQUENCE: 103

```
Met Phe Glu Asp Lys Arg Glu Arg Pro Arg Thr Leu His Glu Leu Cys
 1               5                  10                  15

Glu Ala Leu Asn Val Ser Met His Asn Ile Gln Val Val Cys Val Tyr
             20                  25                  30

Cys Lys Lys Glu Leu Cys Arg Ala Asp Val Tyr Asn Val Ala Phe Thr
         35                  40                  45

Glu Ile Lys Ile Val Tyr Arg Asp Asn Asn Pro Tyr Ala Val Cys Lys
     50                  55                  60
```

```
Gln Cys Leu Leu Phe Tyr Ser Lys Ile Arg Glu Tyr Arg Arg Tyr Ser
 65                  70                  75                  80

Arg Ser Val Tyr Gly Thr Thr Leu Glu Ala Ile Thr Lys Lys Ser Leu
                 85                  90                  95

Tyr Asp Leu Ser Ile Arg Cys His Arg Cys Gln Arg Pro Leu Gly Pro
            100                 105                 110

Glu Glu Lys Gln Lys Leu Val Asp Glu Lys Arg Phe His Glu Ile
        115                 120                 125

Ala Gly Arg Trp Thr Gly Gln Cys Ala Asn Cys Trp Gln Arg Thr Arg
    130                 135                 140

Gln Arg Asn Glu Thr Gln Val
145                 150

<210> SEQ ID NO 104
<211> LENGTH: 151
<212> TYPE: PRT
<213> ORGANISM: Human papillomavirus type 82

<400> SEQUENCE: 104

Met Phe Glu Asp Ile Arg Glu Arg Pro Arg Thr Leu His Glu Leu Cys
  1               5                  10                  15

Glu Ala Cys Asn Thr Ser Met His Asn Ile Gln Val Leu Cys Val Tyr
                 20                  25                  30

Cys Lys Lys Glu Leu Cys Arg Ala Asp Val Tyr Asn Val Ala Phe Thr
            35                  40                  45

Glu Leu Arg Ile Val Tyr Arg Asp Asn Thr Pro Tyr Ala Ala Cys Lys
 50                  55                  60

Lys Cys Leu Met Phe Tyr Ser Arg Ile Arg Glu Tyr Arg Arg Tyr Ser
 65                  70                  75                  80

Arg Ser Val Tyr Gly Ala Thr Leu Glu Ala Ile Thr Asn Lys Ser Leu
                 85                  90                  95

Tyr Glu Leu Leu Ile Arg Cys His Arg Cys Gln Arg Pro Leu Gly Pro
            100                 105                 110

Glu Glu Lys Gln Lys Val Val Asp Asp Lys Lys Arg Phe His Glu Ile
        115                 120                 125

Ala Gly Arg Trp Thr Gly Gln Cys Ala Asn Cys Arg Lys Pro Pro Arg
    130                 135                 140

Gln Arg Ser Glu Thr Gln Val
145                 150

<210> SEQ ID NO 105
<211> LENGTH: 146
<212> TYPE: PRT
<213> ORGANISM: Human papillomavirus type 52

<400> SEQUENCE: 105

Met Phe Glu Asp Pro Ala Thr Arg Pro Arg Thr Leu His Glu Leu Cys
  1               5                  10                  15

Glu Val Leu Glu Glu Ser Val His Glu Ile Arg Leu Gln Cys Val Gln
                 20                  25                  30

Cys Lys Lys Glu Leu Gln Arg Arg Glu Val Tyr Lys Phe Leu Phe Thr
            35                  40                  45

Asp Leu Arg Ile Val Tyr Arg Asp Asn Asn Pro Tyr Gly Val Cys Ile
 50                  55                  60

Met Cys Leu Arg Phe Leu Ser Lys Ile Ser Glu Tyr Arg His Tyr Gln
 65                  70                  75                  80
```

Tyr Ser Leu Tyr Gly Lys Thr Leu Glu Glu Arg Val Lys Lys Pro Leu
                85                  90                  95

Ser Glu Ile Thr Ile Arg Cys Ile Ile Cys Gln Thr Pro Leu Cys Pro
            100                 105                 110

Glu Glu Lys Glu Arg His Val Asn Ala Asn Lys Arg Phe His Asn Ile
        115                 120                 125

Met Gly Arg Trp Thr Gly Arg Cys Ser Glu Cys Trp Arg Pro Arg Pro
    130                 135                 140

Val Thr
145

<210> SEQ ID NO 106
<211> LENGTH: 149
<212> TYPE: PRT
<213> ORGANISM: Human papillomavirus type 58

<400> SEQUENCE: 106

Met Phe Gln Asp Ala Glu Glu Lys Pro Arg Thr Leu His Asp Leu Cys
1               5                   10                  15

Gln Ala Leu Glu Thr Ser Val His Glu Ile Leu Lys Cys Val Glu
            20                  25                  30

Cys Lys Lys Thr Leu Gln Arg Ser Glu Val Tyr Asp Phe Val Phe Ala
        35                  40                  45

Asp Leu Arg Ile Val Tyr Arg Asp Gly Asn Pro Phe Ala Val Cys Lys
    50                  55                  60

Val Cys Leu Arg Leu Leu Ser Lys Ile Ser Glu Tyr Arg His Tyr Asn
65                  70                  75                  80

Tyr Ser Leu Tyr Gly Asp Thr Leu Glu Gln Thr Leu Lys Lys Cys Leu
                85                  90                  95

Asn Glu Ile Leu Ile Arg Cys Ile Ile Cys Gln Arg Pro Leu Cys Pro
            100                 105                 110

Gln Glu Lys Lys Arg His Val Asp Leu Asn Lys Arg Phe His Asn Ile
        115                 120                 125

Ser Gly Arg Trp Thr Gly Arg Cys Ala Val Cys Trp Arg Pro Arg Arg
    130                 135                 140

Arg Gln Thr Gln Val
145

<210> SEQ ID NO 107
<211> LENGTH: 149
<212> TYPE: PRT
<213> ORGANISM: Human papillomavirus type 33

<400> SEQUENCE: 107

Met Phe Gln Asp Thr Glu Glu Lys Pro Arg Thr Leu His Asp Leu Cys
1               5                   10                  15

Gln Ala Leu Glu Thr Thr Ile His Asn Ile Glu Leu Gln Cys Val Glu
            20                  25                  30

Cys Lys Lys Pro Leu Gln Arg Ser Glu Val Tyr Asp Phe Ala Phe Ala
        35                  40                  45

Asp Leu Thr Val Val Tyr Arg Glu Gly Asn Pro Phe Gly Ile Cys Lys
    50                  55                  60

Leu Cys Leu Arg Phe Leu Ser Lys Ile Ser Glu Tyr Arg His Tyr Asn
65                  70                  75                  80

Tyr Ser Val Tyr Gly Asn Thr Leu Glu Gln Thr Val Lys Lys Pro Leu
                85                  90                  95

```
Asn Glu Ile Leu Ile Arg Cys Ile Ile Cys Gln Arg Pro Leu Cys Pro
                100                 105                 110

Gln Glu Lys Lys Arg His Val Asp Leu Asn Lys Arg Phe His Asn Ile
            115                 120                 125

Ser Gly Arg Trp Ala Gly Arg Cys Ala Ala Cys Trp Arg Ser Arg Arg
        130                 135                 140

Arg Glu Thr Ala Leu
145
```

<210> SEQ ID NO 108
<211> LENGTH: 149
<212> TYPE: PRT
<213> ORGANISM: Human papillomavirus type 31

<400> SEQUENCE: 108

```
Met Phe Lys Asn Pro Ala Glu Arg Pro Arg Lys Leu His Glu Leu Ser
1               5                   10                  15

Ser Ala Leu Glu Ile Pro Tyr Asp Glu Leu Arg Leu Asn Cys Val Tyr
            20                  25                  30

Cys Lys Gly Gln Leu Thr Glu Thr Glu Val Leu Asp Phe Ala Phe Thr
        35                  40                  45

Asp Leu Thr Ile Val Tyr Arg Asp Asp Thr Pro His Gly Val Cys Thr
    50                  55                  60

Lys Cys Leu Arg Phe Tyr Ser Lys Val Ser Glu Phe Arg Trp Tyr Arg
65                  70                  75                  80

Tyr Ser Val Tyr Gly Thr Thr Leu Glu Lys Leu Thr Asn Lys Gly Ile
                85                  90                  95

Cys Asp Leu Leu Ile Arg Cys Ile Thr Cys Gln Arg Pro Leu Cys Pro
                100                 105                 110

Glu Glu Lys Gln Arg His Leu Asp Lys Lys Lys Arg Phe His Asn Ile
            115                 120                 125

Gly Gly Arg Trp Thr Gly Arg Cys Ile Ala Cys Trp Arg Arg Pro Arg
        130                 135                 140

Thr Glu Thr Gln Val
145
```

<210> SEQ ID NO 109
<211> LENGTH: 149
<212> TYPE: PRT
<213> ORGANISM: Human papillomavirus type 35

<400> SEQUENCE: 109

```
Met Phe Gln Asp Pro Ala Glu Arg Pro Tyr Lys Leu His Asp Leu Cys
1               5                   10                  15

Asn Glu Val Glu Glu Ser Ile His Glu Ile Cys Leu Asn Cys Val Tyr
            20                  25                  30

Cys Lys Gln Glu Leu Gln Arg Ser Glu Val Tyr Asp Phe Ala Cys Tyr
        35                  40                  45

Asp Leu Cys Ile Val Tyr Arg Glu Gly Gln Pro Tyr Gly Val Cys Met
    50                  55                  60

Lys Cys Leu Lys Phe Tyr Ser Lys Ile Ser Glu Tyr Arg Trp Tyr Arg
65                  70                  75                  80

Tyr Ser Val Tyr Gly Glu Thr Leu Glu Lys Gln Cys Asn Lys Gln Leu
                85                  90                  95

Cys His Leu Leu Ile Arg Cys Ile Thr Cys Gln Lys Pro Leu Cys Pro
                100                 105                 110
```

```
Val Glu Lys Gln Arg His Leu Glu Glu Lys Lys Arg Phe His Asn Ile
            115                 120                 125

Gly Gly Arg Trp Thr Gly Arg Cys Met Ser Cys Trp Lys Pro Thr Arg
        130                 135                 140

Arg Glu Thr Glu Val
145

<210> SEQ ID NO 110
<211> LENGTH: 158
<212> TYPE: PRT
<213> ORGANISM: Human papillomavirus type 18

<400> SEQUENCE: 110

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val
145                 150                 155

<210> SEQ ID NO 111
<211> LENGTH: 98
<212> TYPE: PRT
<213> ORGANISM: Human papillomavirus type 16

<400> SEQUENCE: 111

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 112
<211> LENGTH: 104
```

```
<212> TYPE: PRT
<213> ORGANISM: Human papillomavirus type 18

<400> SEQUENCE: 112

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
                20                  25                  30

Asp Ser Glu Glu Glu Asn Asp Glu Ile Asp Gly Val Asn His Gln His
            35                  40                  45

Leu Pro Ala Arg Arg Ala Glu Pro Gln Arg His Met Leu Cys Met Cys
50                  55                  60

Cys Lys Cys Glu Ala Arg Ile Lys Leu Val Val Glu Ser Ser Ala Asp
65                  70                  75                  80

Asp Leu Arg Ala Phe Gln Gln Leu Phe Leu Asn Thr Leu Ser Phe Val
                85                  90                  95

Cys Pro Trp Cys Ala Ser Gln Gln
            100

<210> SEQ ID NO 113
<211> LENGTH: 98
<212> TYPE: PRT
<213> ORGANISM: Human papillomavirus type 31

<400> SEQUENCE: 113

Met Arg Gly Glu Thr Pro Thr Leu Gln Asp Tyr Val Leu Asp Leu Gln
1               5                   10                  15

Pro Lys Ala Thr Asp Leu His Cys Tyr Glu Gln Leu Pro Asp Ser Ser
                20                  25                  30

Asp Glu Glu Asp Val Ile Asp Ser Pro Ala Gly Gln Ala Lys Pro Asp
            35                  40                  45

Thr Ser Asn Tyr Asn Ile Val Thr Phe Cys Cys Gln Cys Glu Ser Thr
50                  55                  60

Leu Arg Leu Cys Val Gln Ser Thr Gln Val Asp Ile Arg Ile Leu Gln
65                  70                  75                  80

Glu Leu Leu Met Gly Ser Phe Gly Ile Val Cys Pro Asn Cys Ser Thr
                85                  90                  95

Arg Leu

<210> SEQ ID NO 114
<211> LENGTH: 97
<212> TYPE: PRT
<213> ORGANISM: Human papillomavirus type 33

<400> SEQUENCE: 114

Met Arg Gly His Lys Pro Thr Leu Lys Glu Tyr Val Leu Asp Leu Tyr
1               5                   10                  15

Pro Glu Pro Thr Asp Leu Tyr Cys Tyr Glu Gln Leu Ser Asp Ser Ser
                20                  25                  30

Asp Glu Asp Glu Gly Leu Asp Arg Pro Asp Gly Gln Ala Gln Pro Ala
            35                  40                  45

Thr Ala Asp Tyr Tyr Ile Val Thr Cys Cys His Thr Cys Asn Thr Thr
50                  55                  60

Val Arg Leu Cys Val Asn Ser Thr Ala Ser Asp Leu Arg Thr Ile Gln
65                  70                  75                  80

Gln Leu Leu Met Gly Thr Val Asn Ile Val Cys Pro Thr Cys Ala Gln
                85                  90                  95
```

Gln

<210> SEQ ID NO 115
<211> LENGTH: 99
<212> TYPE: PRT
<213> ORGANISM: Human papillomavirus type 35

<400> SEQUENCE: 115

Met His Gly Glu Ile Thr Thr Leu Gln Asp Tyr Val Leu Asp Leu Glu
1               5                   10                  15

Pro Glu Ala Thr Asp Leu Tyr Cys Tyr Glu Gln Leu Cys Asp Ser Ser
            20                  25                  30

Glu Glu Glu Glu Asp Thr Ile Asp Gly Pro Ala Gly Gln Ala Lys Pro
        35                  40                  45

Asp Thr Ser Asn Tyr Asn Ile Val Thr Ser Cys Cys Lys Cys Glu Ala
    50                  55                  60

Thr Leu Arg Leu Cys Val Gln Ser Thr His Ile Asp Ile Arg Lys Leu
65                  70                  75                  80

Glu Asp Leu Leu Met Gly Thr Phe Gly Ile Val Cys Pro Gly Cys Ser
                85                  90                  95

Gln Arg Ala

<210> SEQ ID NO 116
<211> LENGTH: 102
<212> TYPE: PRT
<213> ORGANISM: Human papillomavirus type 39

<400> SEQUENCE: 116

Met Arg Gly Pro Lys Pro Thr Leu Gln Glu Ile Val Leu Asp Leu Cys
1               5                   10                  15

Pro Tyr Asn Glu Ile Gln Pro Val Asp Leu Val Cys His Glu Gln Leu
            20                  25                  30

Gly Glu Ser Glu Asp Glu Ile Asp Glu Pro Asp His Ala Val Asn His
        35                  40                  45

Gln His Gln Leu Leu Ala Arg Arg Asp Glu Pro Gln Arg His Thr Ile
    50                  55                  60

Gln Cys Ser Cys Cys Lys Cys Asn Asn Thr Leu Gln Leu Val Val Glu
65                  70                  75                  80

Ala Ser Arg Asp Thr Leu Arg Gln Leu Gln Gln Leu Phe Met Asp Ser
                85                  90                  95

Leu Gly Phe Val Cys Pro
            100

<210> SEQ ID NO 117
<211> LENGTH: 102
<212> TYPE: PRT
<213> ORGANISM: Human papillomavirus type 45

<400> SEQUENCE: 117

Met His Gly Pro Arg Glu Thr Leu Gln Glu Ile Val Leu His Leu Glu
1               5                   10                  15

Pro Gln Asn Glu Leu Asp Pro Val Asp Leu Leu Cys Tyr Glu Gln Leu
            20                  25                  30

Ser Glu Ser Glu Glu Glu Asn Asp Glu Ala Asp Gly Val Ser His Ala
        35                  40                  45

Gln Leu Pro Ala Arg Arg Ala Glu Pro Gln Arg His Lys Ile Leu Cys
    50                  55                  60

```
Val Cys Cys Lys Cys Asp Gly Arg Ile Glu Leu Thr Val Glu Ser Ser
 65                  70                  75                  80

Ala Glu Asp Leu Arg Thr Leu Gln Gln Leu Phe Leu Ser Thr Leu Ser
                 85                  90                  95

Phe Val Cys Pro Trp Cys
            100
```

<210> SEQ ID NO 118
<211> LENGTH: 101
<212> TYPE: PRT
<213> ORGANISM: Human papillomavirus type 51

<400> SEQUENCE: 118

```
Met Arg Gly Asn Val Pro Gln Leu Lys Asp Val Val Leu His Leu Thr
  1               5                  10                  15

Pro Gln Thr Glu Ile Asp Leu Gln Cys Tyr Glu Gln Phe Asp Ser Ser
                 20                  25                  30

Glu Glu Glu Asp Glu Val Asp Asn Met Arg Asp Gln Leu Pro Glu Arg
             35                  40                  45

Arg Ala Gly Gln Ala Thr Cys Tyr Arg Ile Glu Ala Pro Cys Cys Arg
 50                  55                  60

Cys Ser Ser Val Val Gln Leu Ala Val Glu Ser Ser Gly Asp Thr Leu
 65                  70                  75                  80

Arg Val Val Gln Gln Met Leu Met Gly Glu Leu Ser Leu Val Cys Pro
                 85                  90                  95

Cys Cys Ala Asn Asn
            100
```

<210> SEQ ID NO 119
<211> LENGTH: 99
<212> TYPE: PRT
<213> ORGANISM: Human papillomavirus type 52

<400> SEQUENCE: 119

```
Met Arg Gly Asp Lys Ala Thr Ile Lys Asp Tyr Ile Leu Asp Leu Gln
  1               5                  10                  15

Pro Glu Thr Thr Asp Leu His Cys Tyr Glu Gln Leu Gly Asp Ser Ser
                 20                  25                  30

Asp Glu Glu Asp Thr Asp Gly Val Asp Arg Pro Asp Gly Gln Ala Glu
             35                  40                  45

Gln Ala Thr Ser Asn Tyr Tyr Ile Val Thr Tyr Cys His Ser Cys Asp
 50                  55                  60

Ser Thr Leu Arg Leu Cys Ile His Ser Thr Ala Thr Asp Leu Arg Thr
 65                  70                  75                  80

Leu Gln Gln Met Leu Leu Gly Thr Leu Gln Val Val Cys Pro Gly Cys
                 85                  90                  95

Ala Arg Leu
```

<210> SEQ ID NO 120
<211> LENGTH: 104
<212> TYPE: PRT
<213> ORGANISM: Human papillomavirus type 66

<400> SEQUENCE: 120

```
Met His Gly Lys Val Pro Thr Leu Gln Glu Val Ile Leu Glu Leu Ala
  1               5                  10                  15

Pro Gln Thr Glu Ile Asp Leu Gln Cys Asn Glu Gln Leu Asp Ser Ser
```

```
            20                  25                  30
Glu Asp Glu Asp Glu Asp Glu Ile Asp His Leu Leu Glu Arg Pro Gln
        35                  40                  45

Gln Ala Arg Gln Ala Glu Gln His Lys Cys Tyr Leu Ile His Val Pro
    50                  55                  60

Cys Cys Lys Cys Glu Leu Val Val Gln Leu Asp Ile Gln Ser Thr Lys
65                  70                  75                  80

Glu Glu Leu Arg Val Val Gln Gln Leu Leu Met Gly Ala Leu Thr Val
                85                  90                  95

Thr Cys Pro Leu Cys Ala Ser Lys
            100

<210> SEQ ID NO 121
<211> LENGTH: 110
<212> TYPE: PRT
<213> ORGANISM: Human papillomavirus type 68

<400> SEQUENCE: 121

Met His Gly Pro Lys Pro Thr Val Gln Glu Ile Val Leu Glu Leu Cys
1               5                   10                  15

Pro Tyr Asn Glu Ile Gln Pro Val Asp Leu Val Cys His Glu Gln Leu
            20                  25                  30

Gly Asp Ser Asp Asp Glu Ile Asp Glu Pro Asp His Ala Val Asn His
        35                  40                  45

His Gln His Leu Leu Ala Arg Arg Asp Gln Gln Arg His Arg
    50                  55                  60

Ile Gln Cys Leu Cys Cys Lys Cys Asn Lys Ala Leu Gln Leu Val Val
65                  70                  75                  80

Glu Ala Ser Arg Asp Asn Leu Arg Thr Leu Gln Gln Leu Phe Met Asp
                85                  90                  95

Ser Leu Asn Phe Val Cys Pro Trp Cys Ala Thr Glu Thr Gln
            100                 105                 110

<210> SEQ ID NO 122
<211> LENGTH: 92
<212> TYPE: PRT
<213> ORGANISM: Human papillomavirus type 56/57/58

<400> SEQUENCE: 122

Met His Gly Glu Arg Pro Ser Leu Glu Asp Ile Thr Leu Ile Leu Glu
1               5                   10                  15

Glu Ile Pro Glu Ile Val Asp Leu His Cys Asp Glu Gln Phe Asp Asn
            20                  25                  30

Ser Glu Glu Asp Thr Asn Tyr Gln Leu Thr Glu Pro Ala Val Gln Ala
        35                  40                  45

Tyr Gly Val Val Thr Thr Cys Cys Lys Cys His Ser Thr Val Arg Leu
    50                  55                  60

Val Val Glu Cys Gly Ala Ala Asp Ile Arg His Leu Glu Gln Leu Phe
65                  70                  75                  80

Leu Asn Thr Leu Thr Ile Val Cys Pro Arg Cys Val
                85                  90
```